(12) United States Patent
Kouider et al.

(10) Patent No.: US 11,717,204 B2
(45) Date of Patent: Aug. 8, 2023

(54) DECODING THE VISUAL ATTENTION OF AN INDIVIDUAL FROM ELECTROENCEPHALOGRAPHIC SIGNALS

(71) Applicant: NextMind SAS, Paris (FR)

(72) Inventors: Sid Kouider, Paris (FR); Jean-Maurice Leonetti, Saint Michel sur Orge (FR); Nicolas Barascud, Paris (FR); Robin Zerafa, Arceuil (FR)

(73) Assignee: NextMind SAS, Paris (FR)

( * ) Notice: Subject to any disclaimer, the term of this patent is extended or adjusted under 35 U.S.C. 154(b) by 41 days.

(21) Appl. No.: 16/645,294

(22) PCT Filed: Sep. 6, 2018

(86) PCT No.: PCT/EP2018/073961
§ 371 (c)(1),
(2) Date: Mar. 6, 2020

(87) PCT Pub. No.: WO2019/048525
PCT Pub. Date: Mar. 14, 2019

(65) Prior Publication Data
US 2020/0297263 A1    Sep. 24, 2020

(30) Foreign Application Priority Data
Sep. 8, 2017 (FR) ...................... 1758305

(51) Int. Cl.
*A61B 5/16* (2006.01)
*G16H 50/20* (2018.01)
(Continued)

(52) U.S. Cl.
CPC ................ *A61B 5/168* (2013.01); *A61B 5/30* (2021.01); *A61B 5/369* (2021.01); *A61B 5/7246* (2013.01);
(Continued)

(58) Field of Classification Search
CPC ........... A61B 5/168; A61B 5/30; A61B 5/369; A61B 5/378; A61B 5/7246; A61B 5/7264; A61B 5/7267; A61B 5/742; G16H 50/20
See application file for complete search history.

(56) References Cited

U.S. PATENT DOCUMENTS

| 8,391,966 B2 | 3/2013 | Luo et al. |
| 2005/0088617 A1 | 4/2005 | Hsieh et al. |

(Continued)

FOREIGN PATENT DOCUMENTS

| CA | 3075210 A1 | 3/2019 |
| CN | 102047304 A | 5/2011 |

(Continued)

OTHER PUBLICATIONS

Bin, Guangyu, et al. "An online multi-channel SSVEP-based brain-computer interface using a canonical correlation analysis method" 2009, J. Neural Eng., vol. 6 (Year: 2009).*

(Continued)

*Primary Examiner* — Alex M Valvis
*Assistant Examiner* — Anna Roberts
(74) *Attorney, Agent, or Firm* — Schwegman Lundberg & Woessner, P.A.

(57) ABSTRACT

A method for determining the focus of the visual attention of an individual from electroencephalographic signals. At least one visual stimulus to be displayed is generated from at least one graphical object, a visual stimulus being an animated graphical object obtained by applying to a graphical object a temporal succession of elementary transformations that is temporally parameterized by a corresponding modulation signal. From a plurality of electroencephalographic signals produced by the individual focusing his visual attention to one of the visual stimuli, a modulation signal is recon- (Continued)

structed. A visual stimulus corresponding to the modulation signal for which the degree of statistical dependence with the reconstructed modulation signal is higher than a first threshold is identified.

16 Claims, 13 Drawing Sheets

(51) Int. Cl.
  *A61B 5/00* (2006.01)
  *A61B 5/30* (2021.01)
  *A61B 5/369* (2021.01)
(52) U.S. Cl.
  CPC ............ *A61B 5/7264* (2013.01); *A61B 5/742* (2013.01); *G16H 50/20* (2018.01)

(56) References Cited

U.S. PATENT DOCUMENTS

| | | |
|---|---|---|
| 2014/0017645 A1 | 1/2014 | Simpson et al. |
| 2016/0287157 A1 | 10/2016 | Simpson |

FOREIGN PATENT DOCUMENTS

| | | |
|---|---|---|
| CN | 102573619 A | 7/2012 |
| CN | 104825159 A | 8/2015 |
| CN | 111511269 A | 8/2020 |
| FR | 3070852 A1 | 3/2019 |
| FR | 3070852 B1 | 9/2019 |
| JP | 2010257343 A | 11/2010 |
| JP | 2011015788 A | 1/2011 |
| JP | 2013004006 A | 1/2013 |
| JP | 2013507174 A | 3/2013 |
| JP | 2015226723 A | 12/2015 |
| JP | 2020537583 A | 12/2020 |
| JP | 7124090 B2 | 8/2022 |
| JP | 2022163153 | 10/2022 |
| KR | 20200097681 A | 8/2020 |
| TW | 200946078 A | 11/2009 |
| WO | WO-2004100766 A2 | 11/2004 |
| WO | WO-2010016244 A1 | 2/2010 |
| WO | WO-2019048525 A1 | 3/2019 |

OTHER PUBLICATIONS

Kimura, Yosuke, et al. "SSVEP-Based Brain-Computer Interfaces Using FSK-Modulated Visual Stimuli" Oct. 2013, IEEE Transactions on Biomedical Engineering, vol. 60 (10) (Year: 2013).*
G. Bin et al. "An online multi-channel SSVEP-based brain-computer interface using a canonical correlation analysis method" Journal of Neural Engineering, Institute of Physics Publishing; vol. 6, No. 4; Bristol, GB; Aug. 1, 2009 (6 pages).
E. Yin et al. "A Dynamically Optimized SSVEP Brain-Computer Interface (BCI) Speller" IEEE Transactions on Biomedical Engineering, vol. 62, No. 6; Piscataway, NJ, USA; Jun. 1, 2015 (10 pages).
International Search Report issued in International Application No. PCT/EP2018/073961, dated Jan. 7, 2019 (7 pages).
Written Opinion issued in International Application No. PCT/EP2018/073961; dated Jan. 7, 2019 (7 pages).
"International Application Serial No. PCT/EP2018/073961, International Preliminary Report on Patentability dated Mar. 19, 2020", W/ English Translation, 8 pgs.
"Chinese Application Serial No. 201880072508.9, Office Action dated Sep. 28, 2022", w/English Machine Translation, 12 pgs.
"Japanese Application Serial No. 2022-127543, Notification of Reasons for Refusal dated May 30, 2023", w/ English translation, 5 pgs.

* cited by examiner

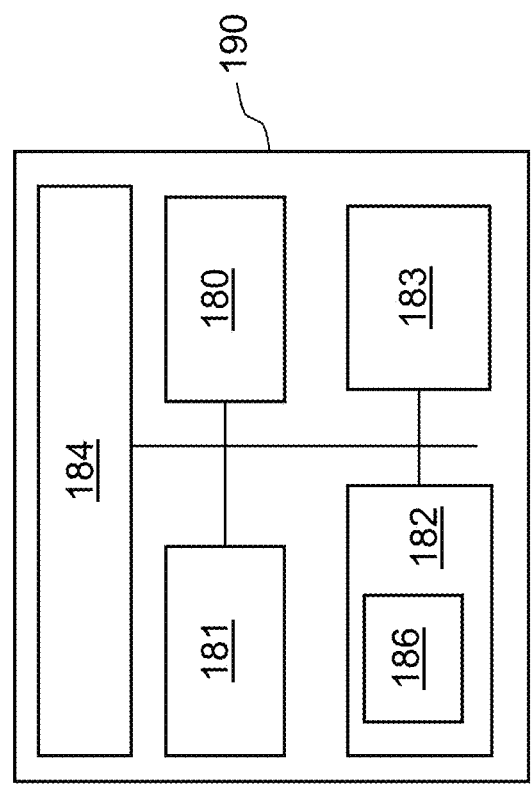

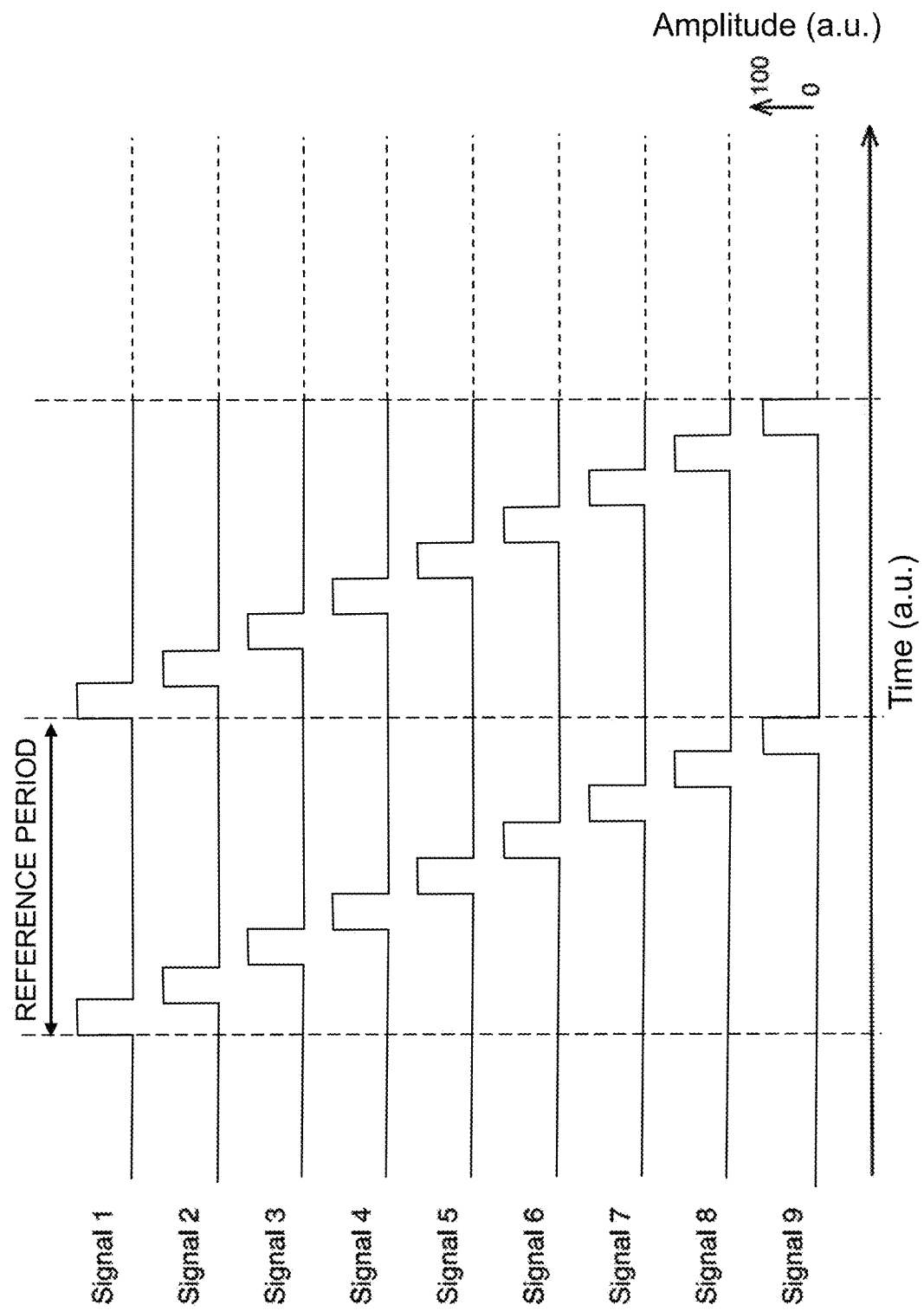

DECODING THE VISUAL ATTENTION OF AN INDIVIDUAL FROM ELECTROENCEPHALOGRAPHIC SIGNALS

TECHNICAL FIELD

The present description relates to a method and system for determining the focus of visual attention of an individual from electroencephalographic signals.

PRIOR ART

The emergence of various portable systems dedicated to recording and exploiting electroencephalographic signals (EEG signals) in multiple applications is observable. In particular, the miniaturization of systems for recording EEG signals and substantial developments in the analysis techniques used for real-time decoding of EEG signals means that new applications may now be envisioned that are both rapid and reliable to use.

Certain decoding techniques are based on an extraction of electro-physiological features from the EEG signals that allow predicting the ongoing relationship between brain activity and visual stimuli in the environment. The difficulty here consists in identifying, in the EEG signal and in real-time, the visual stimulus specific features belonging to the stimulus an individual is attending among a multitude of other visual inputs. Such decoding must be robust, i.e. must allow determining which specific content the individual is attending, in order to be able to trigger a command corresponding to the visual stimulus, with sufficient speed and precision.

Patent document U.S. Pat. No. 8,391,966B2 describes a technique for analyzing EEG signals produced by an individual observing stimuli, each stimulus consisting of a light source flashing at a given frequency. Various features are generated in order to classify the EEG signals into classes corresponding to the different stimuli, with a view to identifying the visual stimulus observed at a given time.

The EEG signals are for example divided into successive segments and correlation coefficients between pairs of segments of a given signal are computed in order to produce a first set of features. An average correlation coefficient is computed then compared to a threshold in order to determine whether the user is observing the stimulus or not. Moreover, the correlation between an EEG signal and the stimulus may be analyzed in order to generate a second set of features: the degree of correlation with a stimulus will be higher if the individual is actually observing this stimulus. The coefficients of an autoregressive model may be computed from an average EEG signal, the model's coefficient forming a third set of features.

This technique assumes prior classification of the EEG by means of a plurality of sets of features in association with a discriminating method based on thresholding, a search for nearest neighbors, neural networks, etc. The technique is therefore dependent on the relevance of the features used and the classification method employed.

Furthermore, the technique is limited to stimuli taking the form of flashing lights, greatly limiting the scope of application.

Other methods are known. For example, the document entitled "An online multi-channel SSVEP-based brain computer interface using canonical correlation analysis method" by Guangyu Bin et al, (Journal of Neural Engineering, IOP Publishing, 2009, uses a modified canonical correlation analysis (CCA) method.

Thus, there appears to be a need for a reliable and real-time EEG decoding technique that is applicable to a brain-machine interface between a user and a software application, for example one comprising text, images and/or menus.

SUMMARY

According to a first aspect, an object of the present description is a method for determining the focus of an individual's visual attention from electroencephalographic signals. The method comprises the generation of a set of at least one visual stimulus to be displayed from at least one graphical object, from at least one elementary transformation and from a set of at least one modulation signal, a visual stimulus being an animated graphical object obtained by applying to a graphical object a temporal succession of elementary transformations that is temporally parameterized by a corresponding modulation signal; reconstructing a modulation signal from a plurality of electroencephalographic signals produced by the individual in order to obtain a reconstructed modulation signal; computing a degree of statistical dependence between the reconstructed modulation signal and each modulation signal of the set of at least one modulation signal; identifying at least one visual stimulus corresponding to a modulation signal for which the degree of statistical dependence is higher than a first threshold.

The method according to the first aspect consists in a hybrid decoding method that combines an approach based on stimulus reconstruction from electroencephalographic (EEG) signals with a method of exciting utilizing one or more stimuli, each having temporal characteristics able to be reproduced in the brain of an individual observing these one or more stimuli, as these temporal characteristics can be found in the EEG signals and therefore can be directly identified within the EEG signals. Such a combination makes it possible both to increase the sensitivity (i.e. the signal-to-noise ratio) of the EEG signal to the generated stimuli and to provide a robust analysis method that is applicable in real-time. The method is applicable to one or more visual stimuli.

Furthermore, the use of elementary transformations (for example a variation in light intensity, a variation in contrast, a colorimetric transformation, a geometric deformation, a rotation, and oscillation, a movement along a path, etc.) allows an extensive range of visual stimuli taking the form of graphical objects to be provided, which opens the door to many applications requiring the distinction to be made between many graphical objects that are presented simultaneously to a user.

The technique is thus adaptable for example to a keyboard display of alphanumeric characters with a view to identifying the alphanumeric character on which the user is attending, or more generally to a display of a plurality of logos, menus, graphical elements, etc. The modulation produced by the modulation signal does not affect viewing comfort provided that the frequency components of this modulation signal are lower than about 25 Hz. A modulation signal for example has a periodic pattern, repeating with a frequency comprised between 2 and 20 Hz, this modulation frequency being sampled at a sampling frequency corresponding to the refresh rate (which in general is higher than 60 Hz) of the monitor used to display the stimuli.

The reconstruction and search for statistical dependence may be carried out in real-time, this allowing the graphical object to which the individual is attending to be identified in real time. In particular, no prior classification of the EEG signals into classes respectively corresponding to the various stimuli is required to reconstruct the modulation signal.

In or more embodiments of the method according to the first aspect, the set of at least one visual stimulus comprises a plurality of visual stimuli and the set of at least one modulation signal comprises a plurality of modulation signals and the method furthermore comprises searching, among the plurality of modulation signals, for a modulation signal which maximizes a degree of statistical dependence with the reconstructed modulation signal; and identifying the visual stimulus corresponding to the modulation signal for which the degree of statistical dependence is maximal; the modulation signals being composed so that an overall degree of statistical dependence, which is determined in the time and/or frequency domain, for all the pairs of modulation signals corresponding to two separate visual stimuli, is lower than a second threshold.

In one more embodiments of the method according to the first aspect, the reconstruction is carried out by applying a reconstruction model to the plurality of electroencephalographic signals.

The reconstruction model establishes the mathematical relationship that exists between a modulation signal used to generate a visual stimulus and the electroencephalographic response of the individual focusing his attention on this visual stimulus. The reconstruction model thus serves to extract from the EEG signals information relevant to a type of stimulus. This relationship is mainly dependent on the position on the skull of an individual (also referred to as the user) of the electrodes of the piece of equipment used to acquire the EEG signals. Specifically, the visual characteristics of the stimuli (type, size, position, color, etc.) have little impact on this relationship.

The reconstruction model may use various, linear or non-linear, mathematical models allowing the EEG signals to be combined, to reconstruct a modulation signal. Because a modulation signal is reconstructed, and not the visual stimulus as such (i.e. the animated graphical object that is displayed on a screen), reconstruction is possible simply and with precision, for example via simple linear combination of the EEG signals, and this without restriction on the nature or semantic content of the animated graphical object used as visual stimulus.

The search for statistical dependence between the reconstructed modulation signal and the one or more various modulation signals is also facilitated. Furthermore, the one or more visual stimuli are displayable on any currently available screen, such as: a computer screen, a tablet screen, a screen of a phone terminal, etc. It is therefore not necessary to provide a dedicated system for producing stimuli. Thus, the use of modulation signals to generate visual stimuli not only allows the reconstruction and search for statistical dependence to be carried out easily, but also makes the method flexible and adaptable to any type of visual stimuli taking the form of an animated graphical object.

In one or more embodiments of the method according to the first aspect, the reconstruction model comprises a plurality of parameters of combination of electroencephalographic signals and the method comprises determining values of the parameters of the plurality of parameters of combination of electroencephalographic signals in an initial learning phase.

In one or more embodiments of the method according to the first aspect, the method furthermore comprises, in the initial learning phase applied to a subset of at least one visual stimulus among the plurality of visual stimuli, obtaining, for each visual stimulus of said subset of at least one visual stimulus, test electroencephalographic signals produced by the individual focusing his attention on the visual stimulus in question; and determining optimal values for the plurality of parameters of combination of electroencephalographic signals, for which values the application of the reconstruction model to the plurality of test electroencephalographic signals recorded for a visual stimulus allows a reconstructed modulation signal to be generated that approximates as best as possible the modulation signal corresponding to the visual stimulus in question.

Thus, by determining the parameters of combination of the EEG signals for a given acquisition device, it is possible to reliably generate a reconstructed modulation signal and to compare it to those used to generate the visual stimuli. Since this relationship is stable over time, and not very dependent on the visual stimuli and on the graphical objects, these parameters of combination of the EEG signals are reusable for all the subsequent visual stimuli liable to be presented to an individual, even if these stimuli are different from those used to, in the learning phase, determine the reconstruction model.

The reconstruction model lastly allows potential variability from one individual to the next to be managed in that the parameters of the reconstruction model may be adjusted for each individual.

According to one or more embodiments, an elementary transformation is a transformation of the set of transformations consisting of a variation in light intensity, a variation in contrast, a colorimetric transformation, a geometric deformation, a rotation, an oscillation, a movement along a path, a change in shape and a change in graphical object or a combination of transformations chosen from said set of transformations.

The subject of the present description, according to a second aspect, is a computer program containing program-code instructions for executing the steps of a method according to the first aspect, when said computer program is executed by a data processor.

The subject of the present description, according to a third aspect, is a computational system comprising at least one memory for storing code instructions of a computer program, configured to execute a method according to the first aspect and at least one data processor configured to execute such a computer program.

The subject of the present description, according to a fourth aspect, is a system for determining the focus of the visual attention of an individual from electroencephalographic signals, the system comprising means for implementing the method according to the first aspect, according to any one of the described embodiments.

The system especially comprises a device for generating display signals, which is configured to generate a set of at least one visual stimulus to be displayed from at least one graphical object, from at least one elementary transformation and from a set of at least one modulation signal, a visual stimulus being an animated graphical object obtained by applying to a graphical object a temporal succession of elementary transformations that is temporally parameterized by a corresponding modulation signal; a signal-processing device configured to obtain a plurality of electroencephalographic signals produced by the individual; obtain a reconstructed modulation signal by reconstructing a modulation signal from the plurality of electroencephalographic signals; compute a degree of statistical dependence between the reconstructed modulation signal and each modulation signal of said set of at least one modulation signal; and identify at least one visual stimulus corresponding to a modulation signal for which the degree of statistical dependence is higher than a first threshold.

According to one or more embodiments of the system according to the fourth aspect, the set of at least one visual stimulus comprises a plurality of visual stimuli and the set of at least one modulation signal comprises a plurality of modulation signals and the signal processing device is furthermore configured to search, among the plurality of modulation signals, for the modulation signal for which the degree of statistical dependence with the reconstructed modulation signal is maximal; identify the visual stimulus corresponding to the modulation signal for which the degree of statistical dependence is maximal; the modulation signals being composed so that an overall degree of statistical dependence, which is determined in the time and/or frequency domain, for all the pairs of modulation signals corresponding to two separate visual stimuli, is lower than a second threshold.

BRIEF DESCRIPTION OF THE FIGS

Other advantages and features of the technique presented above will become apparent on reading the detailed description given below, which makes reference to the FIGS, in which:

FIG. 1A schematically shows a system for determining the focus of the visual attention of an individual from EEG signals according to one example of an embodiment;

FIG. 1B schematically shows a computational device according to one example of an embodiment;

FIG. 2A schematically shows the data and signals exploited in a system and method for determining the focus of visual attention according to one example of an embodiment;

FIGS. 2B-2E each schematically show examples of modulation signals usable in a method or system for determining the focus of visual attention;

FIG. 3 schematically shows aspects of a method and system for determining the focus of visual attention;

In the various embodiments that are described with reference to the FIGS, elements that are similar or identical have been referenced with the same references.

DETAILED DESCRIPTION

The present description is given with reference to functions, functional units, entities, block diagrams and flowcharts that describe various embodiments of methods, systems and programs. Each function, functional unit, entity and step of a flowchart may be implemented by software, hardware, firmware, microcode or any appropriate combination of these technologies. When software is used, the functions, functional units, entities or steps may be implemented by computer-program instructions or software code. These instructions may be stored or transmitted to a computer-readable storage medium and/or be executed by a computer in order to implement these functions, functional units, entities or steps.

The various embodiments and aspects described below may be combined or simplified in multiple ways. In particular, the steps of the various methods may be repeated for each set of graphical objects in question and/or each user in question, the steps may be inverted, executed in parallel and/or executed by various computational entities. Only certain embodiments of examples are described in detail in order to ensure the clarity of the description but these examples are not intended to limit the general scope of the principles that this description considered in its entirety should make clear.

Figure 1A:
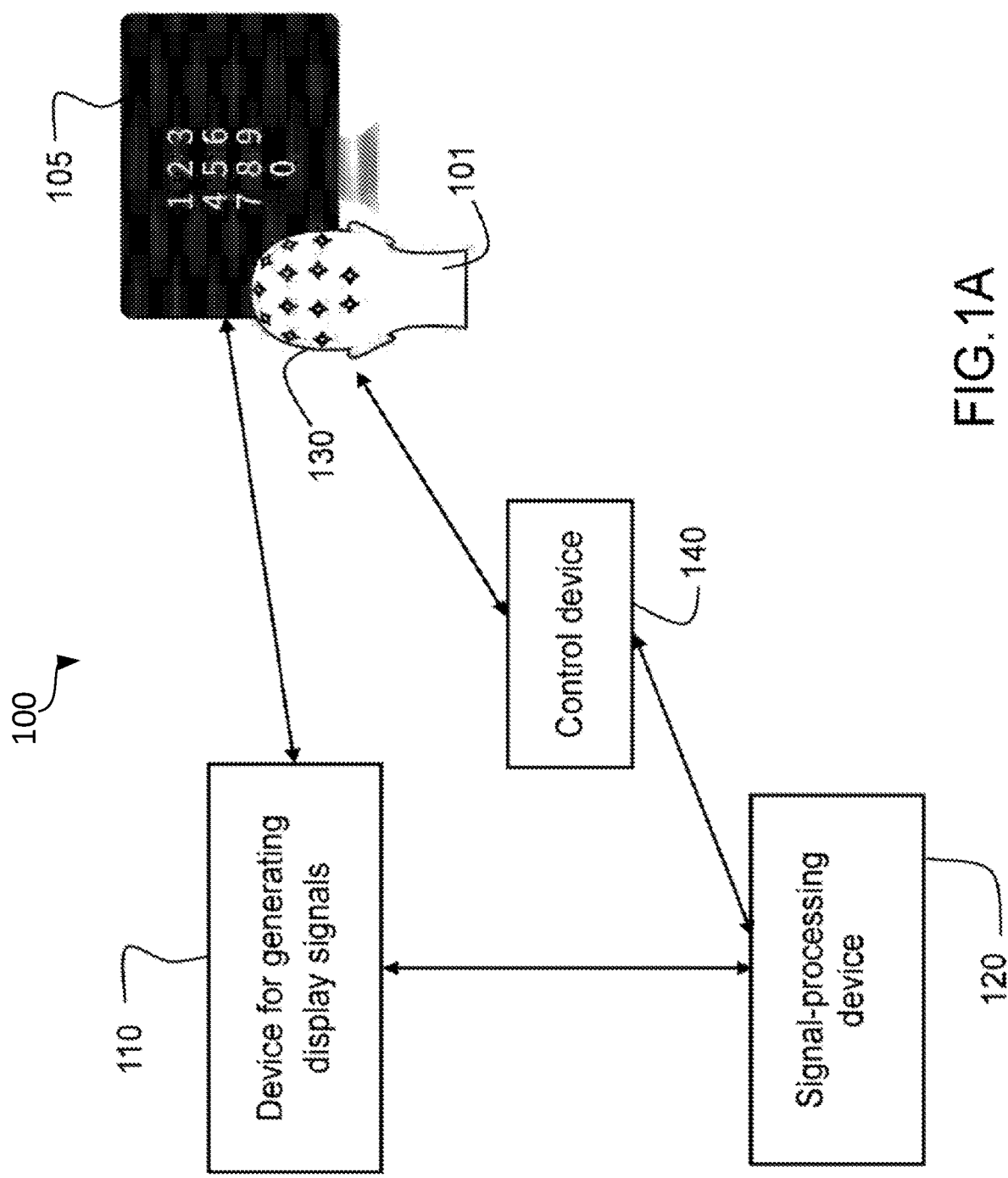

FIG. 1A schematically shows an example of an embodiment of a system 100 for determining the focus of the visual attention of an individual (also referred to as the user below) 101 from electroencephalographic signals.

In one or more embodiments, the system 100 comprises a display screen 105 configured to display animated graphical objects, a device 110 for generating display signals, a signal-processing device 120, a piece of equipment 130 for acquiring EEG signals and a device 140 for controlling the piece of equipment 130.

In one or more embodiments, the device 110 for generating display signals is configured to generate display signals S1, S2, . . . SN, to be displayed by the display screen 105. These display signals encode a plurality of visual stimuli intended to be presented to the user 101 by means of the display screen 105.

In one or more embodiments, the piece of equipment 130 is configured to acquire EEG signals. This piece of equipment for example takes the form of a headcap equipped with electrodes intended to make contact with the skull of the user 101. Such a headcap is for example a headcap manufactured by Biosemi®, which is equipped with 64 electrodes. Other types of equipment are usable: for example the Geodesic™ EEG devices sold by Electrical Geodesics Inc. (EGI)®, or those sold by Compumedics NeuroScan®, which usually count between 16 and 256 electrodes. In the rest of the description, it is assumed, by way of example, that the piece of equipment 130 takes the form of a headcap.

In one or more embodiments, the signal-processing device 120 is configured to process the EEG signals acquired by means of the headcap 130 for acquiring EEG signals.

In one or more embodiments, the device 140 for controlling the piece of equipment 130 is a device that serves as an interface between the headcap 130 and/or the signal-processing device 120. The control device 140 is configured to control the acquisition of EEG signals and to obtain the EEG signals acquired by the headcap 130. In particular, the device 140 for controlling the headcap 130 is configured to send a command to trigger the acquisition of the EEG signals.

All or some of the functions described here with respect to the device 110 for generating display signals, the signal-processing device 120 and the control device 140 may be carried out by software and/or hardware and implemented in at least one computational device comprising a data processor and at least one memory for storing data.

In one or more embodiments, each device 110, 120, 140 and each of the steps of the described methods are implemented by one or more physically separate computational devices. Conversely, the various devices 110, 120, 140 may be integrated into one and the same computational device. Likewise, the steps of the methods described here may be implemented by one and the same computational device.

The piece of equipment 130 for acquiring EEG signals may also comprise a computational device and be configured (data processor, memory, etc.) to implement all or some of the steps of the methods described in this document.

Each computational device has on the whole the architecture of a computer, including the components of such an architecture: one or more data memories, one or more processors, communication buses, one or more user interfaces, one or more hardware interfaces for the connection of this computational device to a network or another piece of equipment, etc.

An example of an embodiment of such an architecture 190 is illustrated in figure IB. This architecture comprises a processing unit 180 including at least one data processor, at least one memory 181, one or more data storage media 182, and hardware interfaces 183 such as network interfaces and interfaces for the connection of peripherals, and at least one user interface 184 including one or more input/output devices such as a mouse, keyboard, display, etc. The data storage medium 182 comprises code instructions of a computer program 186. Such a storage medium 182 may be an optical storage device such as a compact disc (CD, CDR or CD-RW), DVD (DVD-ROM or DVD-RW), a magnetic medium such as a hard disk, a flash memory, a magnetic tape or floppy disk, a removable storage medium such as a USB key, an SD or micro-SD memory card, etc. The memory 181 may be a random-access memory (RAM), a read-only memory (ROM), a cache memory, a non-volatile memory, a backup memory (for example flash or programmable memories), read-only memories or any combination of these types of memory. The processing unit 180 may be any microprocessor, integrated circuit or central processing unit comprising at least one processor based on computational hardware.

Figure 2A:
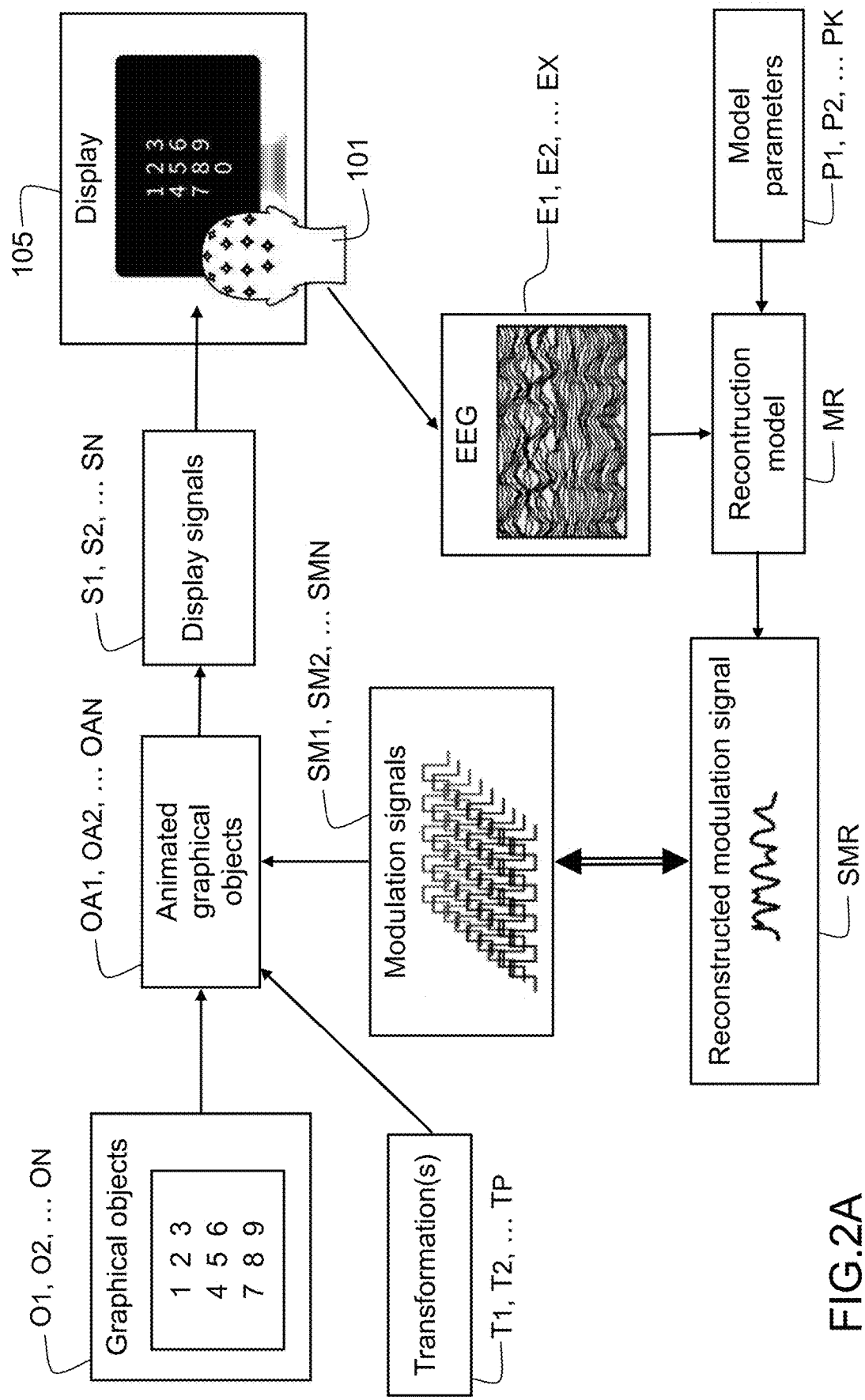

FIG. 2A schematically shows the data and signals exploited in a system and method for determining the focus of visual attention. The corresponding notations will now be introduced.

In one or more embodiments, a plurality of graphical objects O1, O2, . . . , ON intended to be presented to a user 101 is used. Each of these graphical objects may be an alphanumeric character (number or letter or other character), a logo, an image, a text, an element of a user-interface menu, a user-interface button, an avatar, a 3-D object, etc. Each of these graphical objects may be coded via a bitmap or vector image.

In one or more embodiments, one or more elementary transformations T1, T2, . . . , TP are defined in order to be applied to the graphical objects O1, O2, . . . , ON. An elementary transformation may be: a variation in light intensity, a variation in contrast, a colorimetric transformation, a geometric deformation, a rotation, an oscillation, a movement along a planar or three-dimensional path, a change of shape, or even a change of graphical object, etc. A change of graphical object may for example correspond to a transformation that replaces a graphical object with another graphical object of the same category, for example, the replacement of a letter (e.g. A) with another letter (e.g. B), a number with another number, a logo with another logo, etc. An elementary transformation may also be a combination of a plurality of the aforementioned elementary transformations.

Each of these elementary transformations is parameterizable by at least one parameter of application.

In one or more embodiments, a parameter of application defines a degree of transformation of the elementary transformation on a preset scale. A scale from 0 to 100 or from −100 to +100 may for example be used.

For example, when the elementary transformation is a variation in light intensity, this variation in intensity may be applied with a degree of transformation variable between 0 and 100, a degree of transformation equal to 0 meaning that the image coding the graphical object is not modified, and a degree of transformation equal to 100 indicating that the image becomes completely white or, in contrast, black. By making the degree of transformation vary between 0 and 100, an effect is obtained whereby the image appears to flash.

According to another example, when the elementary transformation is a variation in contrast, this variation in contrast may be applied with a degree of transformation variable between 0 and 100, a degree of transformation equal to 0 meaning that the image coding the graphical object is not modified, a degree of transformation equal to 100 indicating that the contrast of the image becomes maximal (the image becomes a black-and-white image, if it is coded in greyscale).

Likewise, for a geometric deformation of morphing type, a degree of transformation may correspond to the degree of morphing. For a rotation, a degree of transformation may corresponding to an angle of rotation. For an oscillation, a degree of transformation may correspond to a rate and/or amplitude of oscillation. For a movement on a path, a degree of transformation may correspond to a distance travelled and/or a speed of movement on the path. For a change of shape (of object category, respectively), a degree of transformation may correspond to a rate and/or amplitude reflecting the passage from one shape (category, respectively) to the other.

For each of the graphical objects O1, O2, . . . , ON, a corresponding modulation signal SM1, SM2, . . . , SMN is generated. A modulation signal serves to define the variations as a function of time in one or more parameters of application of the elementary transformation applied to the graphical object in question. For example, the degree of transformation $di(t)$ at the time t is defined by the amplitude $SMi(t)$ of the modulation signal SMi at the time t.

In one or more embodiments, an animated graphical object OA1, OA2, . . . , OAN is generated for each corresponding graphical object O1, O2, . . . , ON from one or more corresponding elementary transformations and from a corresponding modulation signal. The animated graphical object OA1, OA2, . . . , OAN thus generated is presented on a display screen 105.

In one or more embodiments, a visual stimulus is an animated graphical object OAi (i integer number comprised between 1 and N) obtained by applying to a corresponding graphical object Oi a temporal succession STi of elementary transformations that is temporally parameterized by a corresponding modulation signal SMi. Thus, at each time tz of a discrete sequence of times t0, t1, . . . tz, . . . in a time interval [tmin, tmax], a modified graphical object OAi(tz) is generated, by applying a corresponding elementary transformation Ti to the graphical object Oi with a degree of transformation $di(tz)$ corresponding to the amplitude SMi (tz) at the time tz of the corresponding modulation signal SMi to the graphical object Oi. The animated graphical object thus corresponds to the temporal succession of the modified graphical objects OAi(tz) when tz varies in the time interval [tmin, tmax].

In one or more embodiments, EEG signals, denoted E1, E2, . . . , EX, are acquired by means of a piece of equipment 130 for acquiring EEG signals. From the EEG signals E1, E2, . . . , EX, a reconstructed modulation signal SMR is generated.

In one or more embodiments, the reconstructed modulation signal SMR is generated by applying a reconstruction model MR to the signals E1, E2, ..., EX. The parameters of the reconstruction model MR are denoted P1, P2, ... PK.

The reconstruction model MR may be a linear model, the reconstructed modulation signal being a linear combination of the signals E1, E2, ..., EX.

Other more elaborate models may be used, in particular models based on neural networks.

In one or more embodiments, a modulation signal is composed of elementary signals. These elementary signals may be square-wave signals, triangle-wave signals, sinusoidal signals, etc. The modulation signals may have different durations. In one or more embodiments, the modulation signals are periodic, a temporal pattern being periodically reproduced by each modulation signal. A modulation signal for example has a periodic temporal pattern, repeating with a frequency comprised between 2 and 20 Hz, this modulation signal being sampled at a sampling frequency corresponding to the refresh frequency (which in general is higher than 60 Hz) of the screen on which the visual stimuli (i.e. the animated graphical objects) generated from the modulation signals are displayed.

The amplitude of the modulation signal SMi serves to define a degree of transformation. The relationship between the amplitude of the modulation signal SMi and the degree of transformation may or may not be linear. The amplitude of a modulation signal SMi may vary between a minimum value (corresponding to a 1st° of transformation) and a maximum value (corresponding to a 2nd° of transformation).

In one or more embodiments, the modulation signals are in this case independent pairwise: the modulation signals are composed so that the dependence, measured in the time and/or frequency domain, between any two separate modulation signals is minimal (for example zero) or lower than a given threshold SC1. The dependence between two signals may be quantified by a degree of statistical dependence. The degree of statistical dependence between two modulation signals may be computed, in the time domain, for example via a coefficient of temporal correlation and/or, in the frequency domain, for example via the degree of spectral coherence.

In one or more embodiments, for each pair of modulation signals corresponding to separate visual stimuli, the modulation signals are temporally decorrelated pairwise.

In one or more embodiments, a degree of statistical dependence may be computed for each pair of modulation signals corresponding to separate visual stimuli, then an overall degree of statistical dependence (for example, the average degree of dependence, the maximum degree of dependence or the cumulative degree of dependence) may be computed for all the pairs of modulation signals. The modulation signals are determined by searching for the modulation signals that minimize this overall degree of statistical dependence or that allow an overall degree of statistical dependence that is below a preset threshold SC1 to be obtained.

In one or more embodiments, the degree of statistical dependence computed for each pair of modulation signals corresponding to separate visual stimuli is zero or below a threshold SC1.

In one or more embodiments, the degree of statistical dependence between two modulation signals may be computed to be the coefficient of temporal correlation between these signals, where the correlation coefficient $\rho(X,Y)$ between the two signals X and Y may be obtained using Pearson's formula:

$$\rho(X, Y) = \frac{\mathbb{E}[(X - \mathbb{E}(X))(Y - \mathbb{E}(Y))]}{\sigma_X \sigma_Y} = \frac{\mathbb{E}[XY] - \mathbb{E}[X]\mathbb{E}[Y]}{\sigma_X \sigma_Y}$$

where $\mathbb{E}$ is the expected value of a signal, and $\sigma$ its standard deviation. The coefficient of temporal correlation is comprised between 0 and 1, the value 0 corresponding to temporally decorrelated signals.

The degree of statistical dependence between the modulation signals may be determined via other mathematical criteria, such as Spearman's correlation coefficient or Kendall's correlation coefficient, or replaced by measurements of statistical dependence such as mutual information.

The degree of spectral coherence between two signals x (t) and y (t) is a real-valued function that may be defined for example by the ratio $$|Gxy(f)|^2/(Gxx(f)*Gyy(f))$$

where Gxy (f) is the cross spectral density between x and y, and Gxx (f) and Gyy (f) the power spectral density of x and y, respectively.

In one or more embodiments, the degree of statistical dependence is computed over a reference period, for example corresponding to the duration of the reconstruction window (see step 414) and/or the decoding window (see step 415).

An effective discrimination between the modulation signals is possible when the overall degree of statistical dependence (for example computed to be the average degree of dependence, the maximum degree of dependence or a cumulative degree of dependence), computed for all the pairs of modulation signals corresponding to separate visual stimuli, is zero (for example for temporally decorrelated signals) or lower than a threshold SC1, for example chosen to be equal to 0.2 (i.e. 20% respectively if this degree is expressed in percent). The lower the overall degree of statistical dependence, the easier and more effective the identification of the visual stimulus observed by an individual attending this stimulus will be. The probability of error in discrimination (corresponding to the percentage of cases in which the visual stimulus identified in step 415 is not that to which the individual is actually attending), among the set of modulation signals, of the modulation signal that will serve to generate the visual stimulus observed by the subject, is also correspondingly lower. The threshold SC1 may depend on the choice of the type of modulation signals. In practice, it is possible to set a maximum probability of discrimination error (a probability acceptable for a given application for example), and to adjust the modulation signals so as to remain below this maximum discrimination error rate. It will be understood here that, even in the case where the reconstruction (see step 414) is ideal (i.e. the reconstructed signal is equal at each time to one of the modulation signals SMi), the quality of the decoding (see step 415) depends on the degree of statistical dependence between the modulation signals, because if the modulation signals SMi are entirely dependent, it will be impossible to select one modulation signal SMi rather than another.

Each of FIGS. 2B, 2C, 2D and 2E schematically shows a set of modulation signals usable in a system for determining the focus of visual attention in order to generate visual stimuli.

Figure 2B:
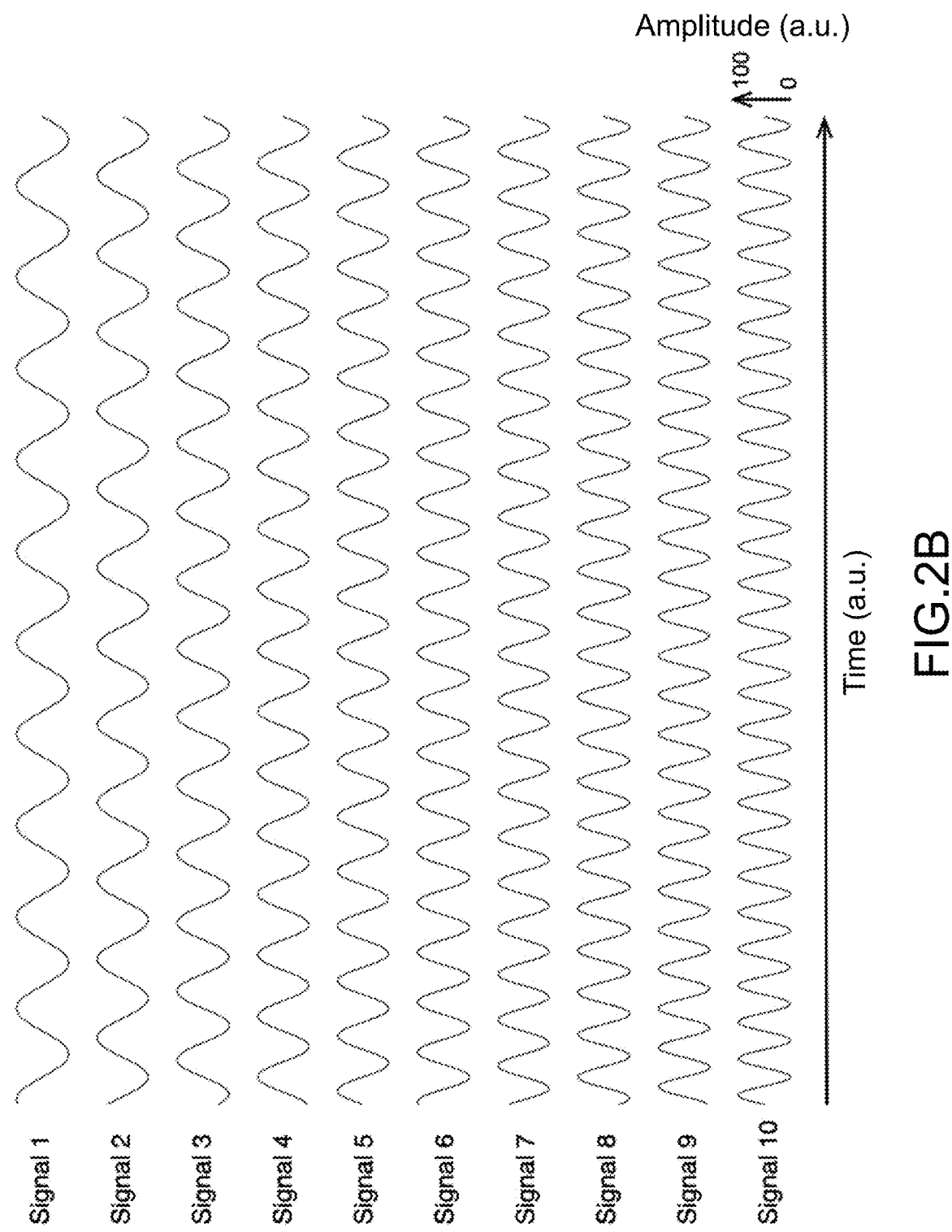

FIG. 2B shows a first exemplary set of 10 modulation signals, signal 1 to signal 10, that are temporally decorrelated pairwise. These 10 signals are periodic sinusoidal signals having different frequencies (and therefore different periods) varying, in steps of 0.2 Hz, between 1 Hz and 2 Hz, such that any two signals in this first set do not have the same frequency. The phases of these signals are unimportant. In the example shown in FIG. 2B, the amplitude of these signals varies between 0% and 100%, meaning that the corresponding degree of transformation varies (with a suitable coefficient of proportionality) between a minimum value and a maximum value. For all the pairs of modulation signals of this set of 10 signals, the degree of spectral overlap is zero (i.e. absence of common frequency components) and the maximum coefficient of temporal correlation in all the pairs of modulation signals is 0.2, this coefficient of temporal correlation being computed in a correlation window of 4 seconds.

Figure 2C:
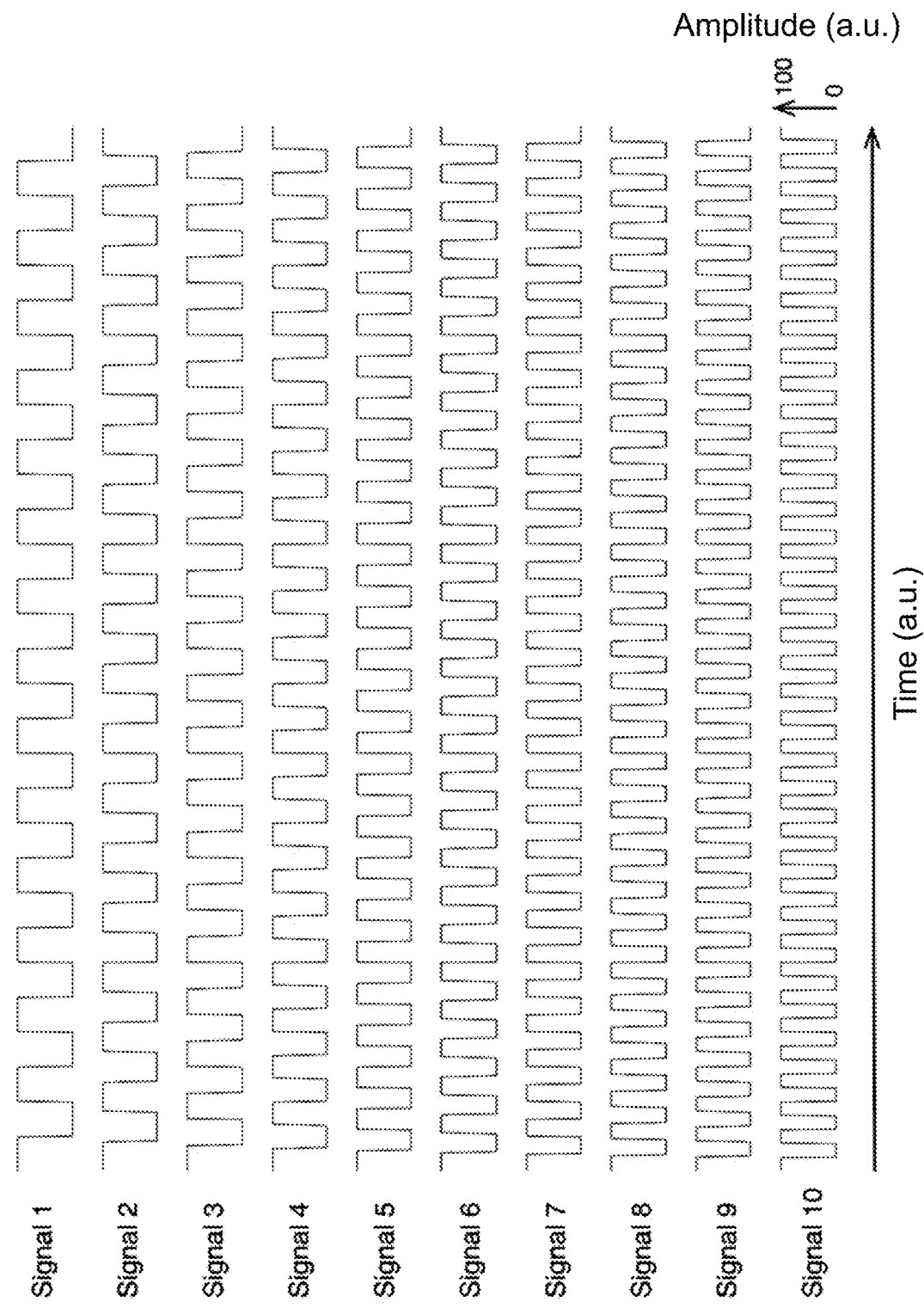

FIG. 2C shows a second exemplary set of 10 modulation signals, signal 1 to signal 10, that are temporally decorrelated pairwise. These 10 signals are periodic square-wave signals having different frequencies (and therefore different periods) varying, in steps of 0.2 Hz, between 1 Hz and 2 Hz, such that any two signals in this second set do not have the same frequency. The phases of these signals are unimportant. As in FIG. 2B, the amplitude of these signals varies between 0% and 100% meaning that the corresponding degree of transformation varies (with a suitable coefficient of proportionality) between a minimum value and a maximum value. For all the pairs of modulation signals of this set of 10 signals, the degree of spectral overlap may be nonzero if certain harmonic components are common but the maximum coefficient of temporal correlation in all the pairs of modulation signals is 0.17, this coefficient of temporal correlation being computed in a correlation window of 4 seconds.

Figure 2D:
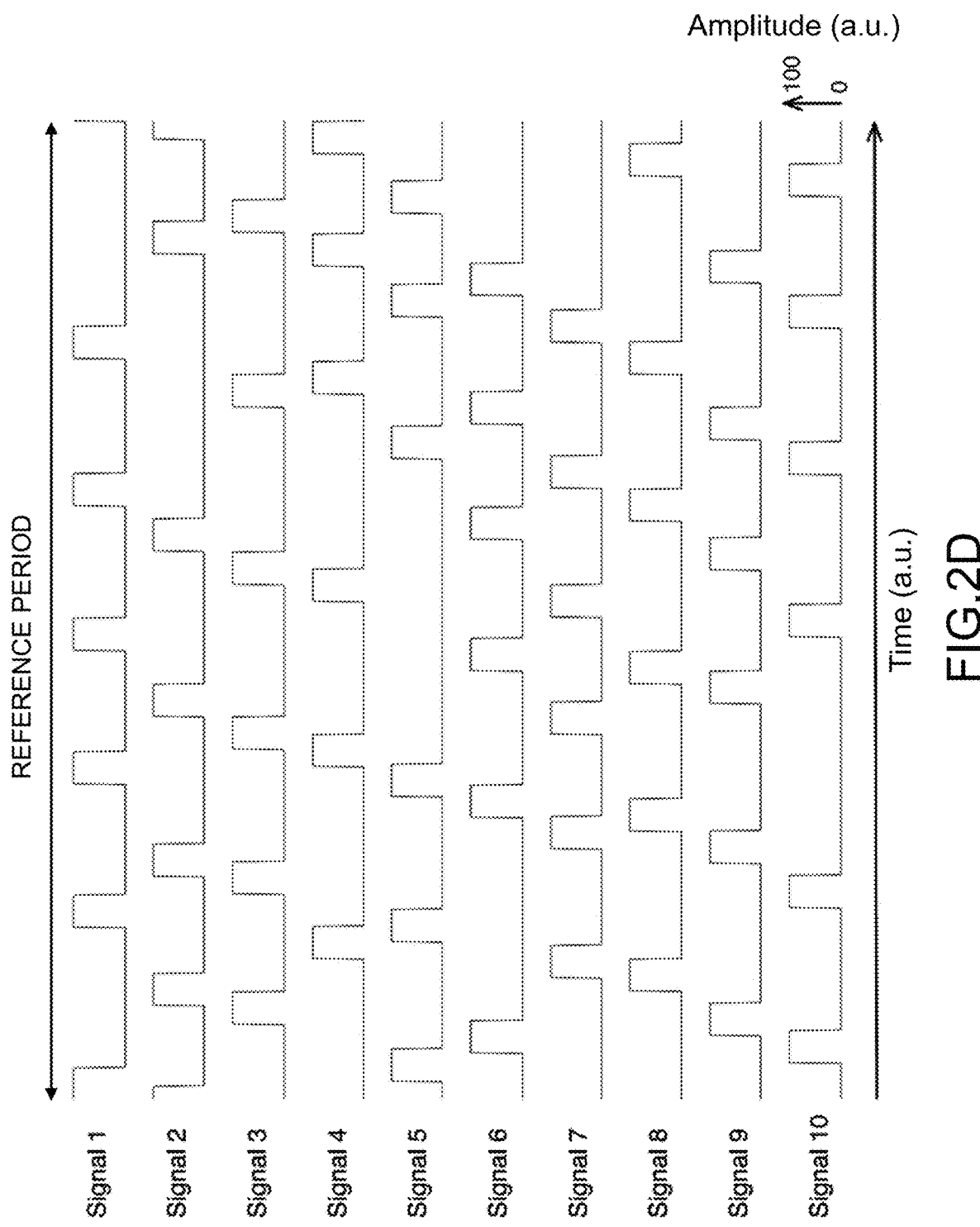

FIG. 2D shows a third exemplary set of 10 modulation signals, signal 1 to signal 10, that are temporally decorrelated pairwise. These 10 signals are periodic signals having the same period (called the reference period in FIG. 2D) and are composed of elementary square-wave signals such that the temporal patterns of any two signals in this third set are different in the reference period. In this case, the phase of each of the signals is important in that it must be adjusted so as to limit the coefficient of temporal correlation, and therefore the degree of statistical dependence, to a maximum value for each pair of separate modulation signals that is selected from this set of 10 modulation signals. As in FIG. 2B, the amplitude of these signals varies between 0% and 100% meaning that the corresponding degree of transformation varies (with a suitable coefficient of proportionality) between a minimum value and a maximum value.

FIG. 2E shows a third exemplary set of 9 modulation signals, signal 1 to signal 9, that are temporally decorrelated pairwise. These signals are periodic signals having the same period (called the reference period in FIG. 2E). Each of the modulation signals comprises a temporal pattern composed of a short square-wave pulse of 100% amplitude followed by a signal of longer duration of 0% amplitude, the square-wave pulses of the various visual modulation signals being offset in time with respect to the others so that, at a given time, one single modulation signal has an amplitude of 100% whereas the others have an amplitude of 0%. These modulation signals all have the same temporal pattern (with a different phase shift) and it is by adjusting the phase of each of the signals that it is possible to control the coefficient of temporal correlation, and therefore the degree of statistical dependence, between two signals. When the transformation function used is a function that changes brightness, the graphical object being visible (unchanged brightness), when the modulation signal is at 100% and invisible when the modulation signal is at 0% (zero brightness), the obtained animated graphical objects, which are obtained from these modulation signals and from this elementary transformation, flash by appearing and disappearing in a given order, a single visual stimulus being visible at a given time. For all the pairs of modulation signals of this set of 10 signals, the coefficient of temporal correlation is zero.

It is therefore possible to obtain temporally decorrelated modulation signals using different frequencies, phases or temporal patterns for each pair of modulation signals, for example:
With signals composed of the same periodic temporal pattern, but having different frequencies and therefore different periods (case of FIGS. 2B and 2C), phase being unimportant;
With signals composed of periodic different temporal patterns that optionally have the same duration (i.e. the same signal period), with specific phases specific to each temporal pattern (case of FIG. 2D);
With signals composed of the same periodic temporal pattern having the same period, but the patterns being phase shifted with respect to one another (case of FIG. 2E).

Figure 3:
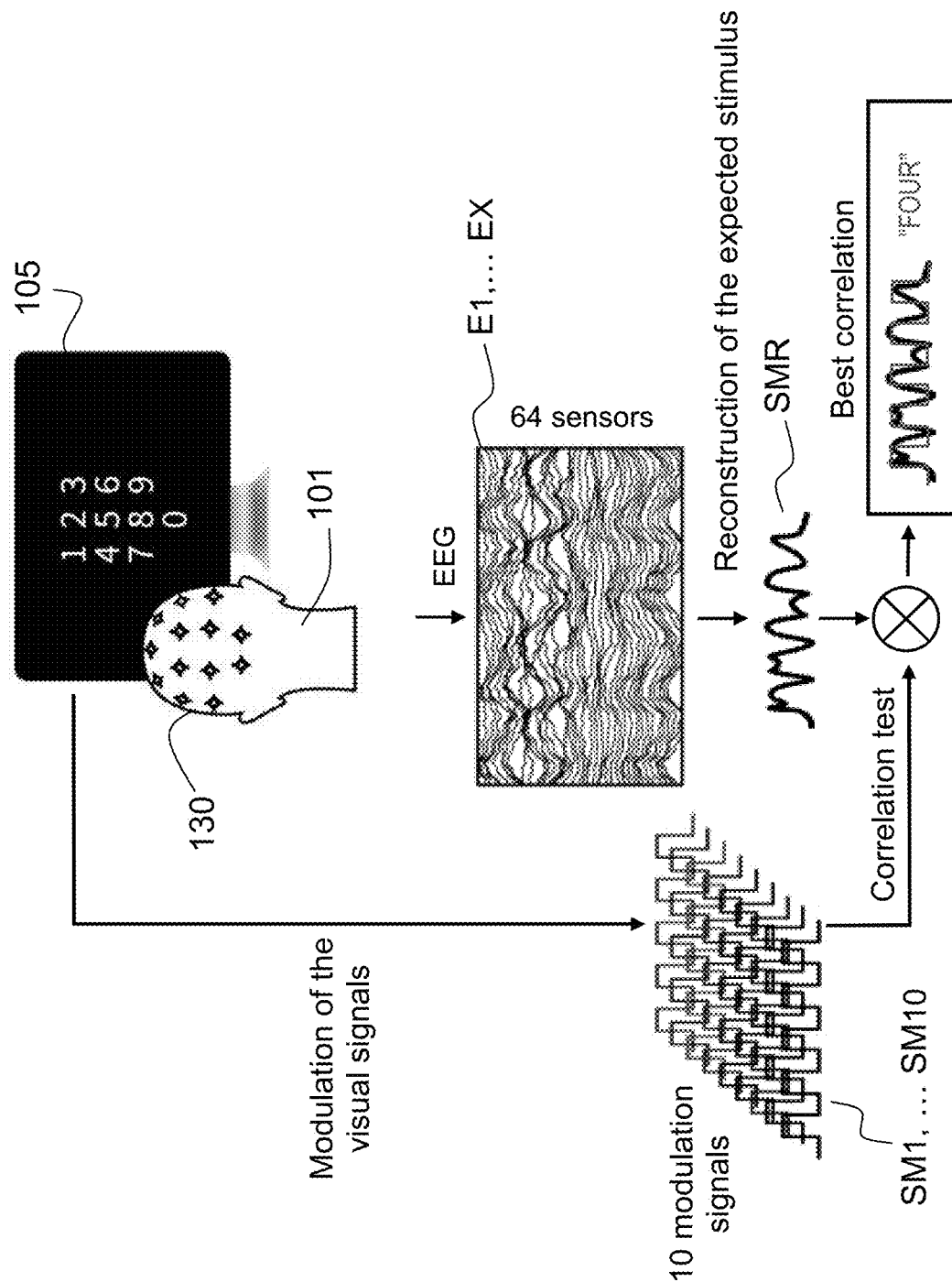

FIG. 3 schematically shows aspects of a method and system for determining the focus of visual attention.

In one or more embodiments, the reconstructed modulation signal SMR is compared to each of the modulation signals SM1, SM2, . . . , SMN in order to seek a modulation signal for which the degree of statistical dependence is maximal. For example, if the degree of statistical dependence is maximal for the modulation signal SM4, this means that the visual attention of an individual is focused on the visual stimulus OA4 generated from this modulation signal SM4.

In the example shown in FIG. 3, the visual stimuli are the numbers 0 to 9, the visual attention of the individual is focused on the number 4 corresponding to visual stimulus OA4. The maximum degree of statistical dependence is found with the corresponding modulation signal SM4.

Figure 4A:
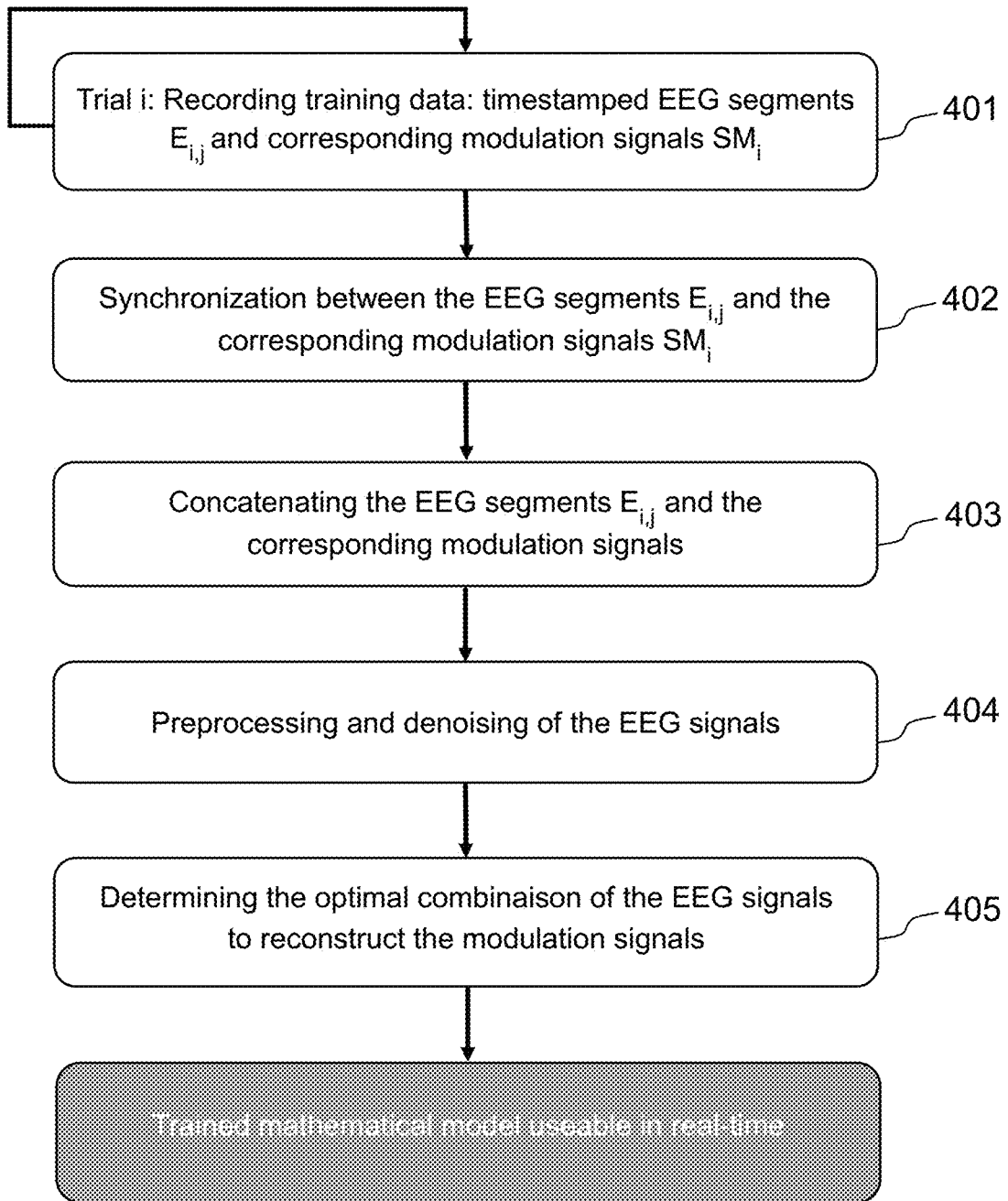
FIG. 4A is a flowchart of a method for generating an EEG signal reconstruction model according to one example of an embodiment.

An example of an embodiment of a method for generating a reconstruction model MR is schematically illustrated in FIG. 4A. Although the steps of this method are presented sequentially, certain at least of the steps may be omitted or indeed be executed in a different order or indeed be executed in parallel or even combined in order to form only a single step.

In a step 401, a trial i ($i \in [1; N]$) is carried out with a visual stimulus generated from a modulation signal SMi: the visual stimulus is presented on a display screen and an individual is invited to observe the visual stimulus, i.e. to turn his visual attention to this visual stimulus. Each visual stimulus is an animated graphical object obtained by applying, to a graphical object, a temporal succession of elementary transformations that is temporally parameterized by a corresponding modulation signal. Test EEG signals $E_{i,j}$ are recorded while the individual is attending the visual stimulus in question, where i is the index identifying the trial and the corresponding modulation signal, j is the index identifying the EEG channel recorded. Each of these EEG signals $E_{i,j}$ is composed of a plurality of EEG segments $E_{i,j,k}$, where k is the index identifying the segment.

In an example of implementation of step 401, ten visual stimuli taking the form of flashing numbers (numbers ranging from 0 to 9) are displayed on a screen, each flashing at a slightly different frequency. The individual is equipped with an EEG headcap and views a display screen on which the ten numbers flash at different frequencies. A succession of trials is carried out. Each trial lasts for example about ten seconds, the interval between two trials for example being 1 or 2 seconds. In each trial, the individual is instructed to attend one of the numbers and must ignore the others until the following trial. The individual thus switches his attention from one stimulus to the next and generates EEG signals E1, E2, ..., EX at different frequencies depending on the focus of his visual attention.

In a first variant embodiment, the EEG segments are time stamped in step 401. The modulation signals are also time stamped in step 401. The time stamping may be carried out using any method.

In this first variant embodiment, the clock of the piece of acquiring equipment 130 is used to timestamp the EEG segments and to produce a time code $t_i'$ for each EEG segment. The clock of the control device 140 is used to timestamp the modulation signals and to produce a time code each time a preset event occurs in the stimulation (for example corresponding to the appearance of a new visual stimulus on the screen or to the start of the display of a stimulus).

In a second variant embodiment, an additional EEG channel is used, via which short electrical pulses of known amplitude are transmitted each time a preset event occurs in the simulation (for example corresponding to the appearance of a new visual stimulus on the screen or to the start of the display of a stimulus). This additional EEG channel containing the short pulses is saved with the segments of EEG data.

Step 401 is repeated a plurality of times, for each visual stimulus of a plurality of visual stimuli, so as to record the corresponding EEG signals produced by the individual when he is attending the visual stimulus in question.

In a step 402, the EEG segments Ei,j,k and the modulation signals SMi are temporally aligned (or synchronized). This synchronization may be carried out using any method.

This synchronization may use the double timestamp of the EEG segments and of the modulation signals, or indeed the additional EEG channel.

When the double timestamp is used, and the time codes are produced using two different clocks, it is necessary to correct these values so as to obtain timestamps produced virtually by the same reference clock, so as to correct for potential temporal drift between the clocks. For example, when the clock of the control device is used as reference clock, the time codes $t_i'$ of the time stamped EEG segments Ei,j,k produced by the clock of the acquiring device are resynchronized with respect to the reference clock to obtain time codes $t_i$. By associating these corrected time codes of the EEG segments with those produced for the modulation signals, it is possible to achieve the alignment between the EEG segments Ei,j,k and the signals SMi.

The difference between the reference clock (t) of the control device 140 and that of the piece of equipment 130 for acquiring the EEG data (t') is modelled by a linear equation: diff=$a^*(t'-t_0)+b=t'-t$, where a is the drift between the two clocks and b is the offset at $t'=t_0$. To estimate these coefficients a and b, a series of x points (t', diff(t')) are acquired, prior to step 401, then the coefficients a and b are estimated using the least-squares method. In order to compensate for random variations in the time taken to execute the instructions and to transmit data between the control device 140 and the piece of acquiring equipment 130, each point (t', diff(t')) is obtained by the control device 140 successively sending n time codes $t_k$ to the piece of acquiring equipment 130, which produces, each time a time code $t_k$ is received, a time code $t_k'$. The point (t', diff(t')) retained for the computation of the coefficients a and b corresponds to the pair ($t_k'$, diff=$t_k'-t_k$) for which the difference ($t_k'-t_k$) is minimal. Once the coefficients a and b have been obtained, the time codes are corrected in the following way:

$$t_i = t_i' - a^*(t_i'-t_0) - b$$

The time stamping and synchronizing steps are however optional and are in particular not necessary when the piece of acquiring equipment 130 and the control device use the same clock.

In a step 403, the EEG segments Ei,j,k are concatenated so as to generate the EEG signals Ei,j.

In a step 404, preprocessing and denoising may be applied to the EEG signals so as to optimize the signal/noise ratio. Specifically, the EEG signals may be considerably contaminated by artefacts both of intra- and extra-cerebral origin, for example electrical artefacts (such as at 50 Hz, frequency of the current of the mains grid in Europe) or biological artefacts (such as eye movements, the electrocardiogram, muscular activity, etc.). In one or more embodiments, the signals E1, E2, ..., EX are thus denoised prior to the generation of the reconstructed modulation signal SMR. This denoising may consist in simply filtering high frequencies from the signals E1, E2, ..., EX, for example all the frequencies higher than 40 Hz in order to remove the electrical noise produced by the mains grid. Multivariate statistical approaches may be used, in particular principal component analysis (PCA), independent component analysis (ICA) and canonical correlation analysis (CCA), allowing the useful components of the EEG signal (i.e. those due to the brain activity related to the cognitive task being carried out) to be separated from the irrelevant components.

In a step 405, the parameters of the reconstruction model are determined. This determination may be carried out so as to minimize the reconstruction error. The reconstruction model for example comprises a plurality of parameters of combination of EEG signals. These parameters of combination are determined using a method of solving mathematical equations so as to determine optimal values for the parameters of combination, i.e. the values for which the application of the reconstruction model to the plurality of test EEG signals Ei,j recorded for a visual stimulus allows a reconstructed modulation signal to be generated that approximates as best as possible the modulation signal corresponding to the visual stimulus in question, i.e. the values for which the reconstruction error is minimal.

In one or more embodiments, the values $\alpha_j$ of the parameters of combination may be fixed (independent of time). In other embodiments, these values may be adjusted in real-time in order to take into account a potential adaptation of the brain activity of the user 101, or a variation in the signal/noise ratio in the EEG signal during a recording session.

The reconstruction model MR may be a linear model that produces a modulation signal via linear combination of the signals Ei,j. In this case, the parameters of combination are parameters $\alpha_j$ of linear combination and the mathematical equations are linear equations of the form:

$$SMi = \Sigma_j \alpha_j Ei,j \text{ for } i \in [1;N]$$

Other more elaborate models may be used, in particular models based on neural networks, with which the modulation signal is obtained by applying, in cascade, non-linear mathematical operations to the signals Ei,j. For example, a Siamese network, in which a neural network is trained (on the basis of calibration data) to make any EEG signal E correspond to a one-dimensional time signal R (in the present case, a modulation signal) so that, two EEG signals E1 and E2 recorded at different times respectively produce one-dimensional signals R1 and R2 (in the present case, modulation signals) that are similar when the attention of the individual is focused on the same animated graphical object, and dissimilar when the attention of the individual is focused on two separate animated graphical objects. The notion of similarity between two signals is defined in the mathematical sense (it may for example be a question of a simple correlation) and corresponds to a function that quantifies the degree of similarity between two objects (see for example the page: https://en.wikipedia.org/wiki/Similarity_measure). A plurality of mathematical definitions of similarity may be used, such as for example the inverse of the Euclidean distance, or even the "cosine similarity" (see for example the page: https://en.wikipedia.org/wiki/Cosine_similarity).

The reconstructed modulation signal is a one-dimensional signal R generated by the neural network from a newly acquired EEG sample E.

In one or more embodiments, the steps of the method for generating a reconstruction model are implemented by a system 100 according to FIG. 1A, for example by the signal-processing device 120.

Figure 4B:
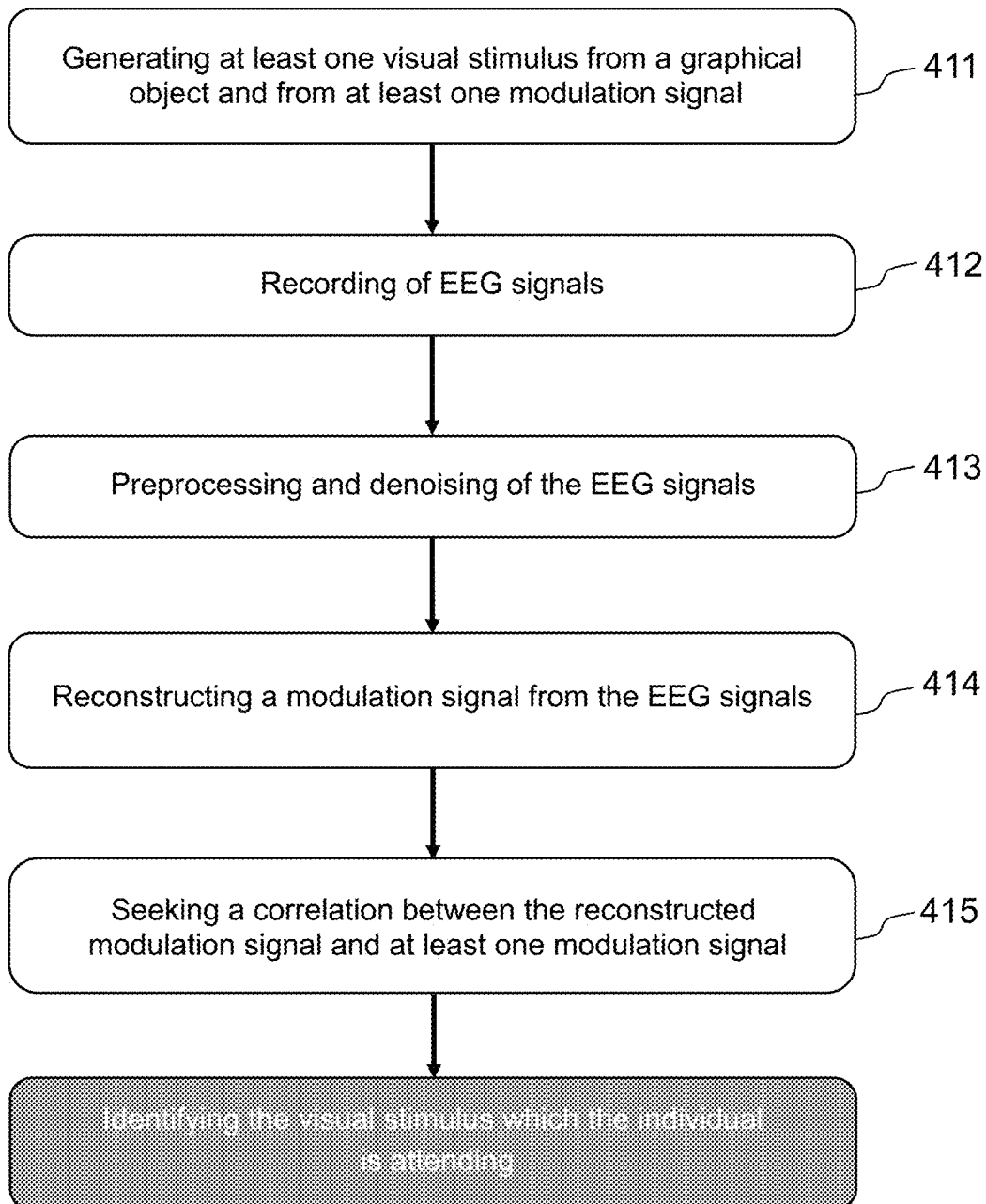
FIG. 4B is a flowchart of a method for determining the focus of the visual attention of an individual according to one example of an embodiment.

An example of an embodiment of a method for determining the focus of the visual attention of an individual is schematically illustrated in FIG. 4B. Although the steps of this method are presented sequentially, certain at least of these steps may be omitted or indeed be executed in a different order or indeed be executed in parallel or even combined to form only a single step.

In one or more embodiments, the steps of the method for determining the focus of visual attention are implemented by a system 100 according to FIG. 1A, for example by the signal-processing device 120 and the device 110 for generating display signals.

In a step 411, the device 110 for generating display signals is configured to generate a plurality of visual stimuli from a plurality of graphical objects O1, O2, . . . , ON, from a plurality of elementary transformations T1, T2, . . . , TP and from a plurality of modulation signals SM1, SM2, . . . , SMN. A visual stimulus is an animated graphical object OAi (i comprised between 1 and N) obtained by applying to a corresponding graphical object Oi a temporal sequence STi of elementary transformations that is temporally parameterized by a corresponding modulation signal SMi.

In one or more embodiments, the number N of visual stimuli, of modulation signals and of graphical objects is equal to 1.

In one or more embodiments, the number P of elementary transformations is equal to 1. Each elementary transformation of the temporal sequence STi of elementary transformations may thus correspond to a given elementary transformation a parameter of application of which varies over time.

Over time, the individual may pass his visual attention from one animated graphical object to another. During this time, in a step 412, the electroencephalographic signals E1, E2, . . . , Ej, . . . , EX produced by the individual are recorded by the piece of acquiring equipment 130.

In one or more embodiments, the signal-processing device 120 is configured to obtain a plurality of electroencephalographic signals E1, E2, . . . , Ej, . . . , EX produced by the individual focusing his attention on one of the visual stimuli OAi.

In a step 413, the electroencephalographic signals E1, E2, . . . Ej, . . . EX are preprocessed and denoised so as to improve the reliability of the method for determining the focus of visual attention. The preprocessing may consist in synchronizing the segments of electroencephalographic signals E1, E2, . . . Ej, . . . EX with respect to a reference clock, as explained above with respect to step 402, in concatenating the segments of electroencephalographic signals as explained above with respect to step 403, and/or in denoising the electroencephalographic signals as explained above with respect to step 404.

In one or more embodiments, the signal-processing device 120 is configured, in a step 414, to obtain a reconstructed modulation signal SMR by reconstructing a modulation signal from a plurality of electroencephalographic signals E1, E2, . . . , Ej, . . . , EX.

In one or more embodiments, the signal-processing device 120 is configured to reconstruct a modulation signal and to generate a reconstructed modulation signal SMR from the plurality of electroencephalographic signals obtained in step 413 or 412 (with or without preprocessing and/or denoising). In one or more embodiments, the reconstruction is carried out by applying a reconstruction model to the plurality of electroencephalographic signals obtained in step 413 or 412 (with or without preprocessing and/or denoising). This reconstruction may be carried out in a given moving time window, here called the reconstruction window, and periodically repeated for each temporal position of the reconstruction window.

For example, when the reconstruction model MR is a linear model that produces a modulation signal via a linear combination of the signals E1, E2, Ej, . . . , EX. In this case, the parameters of combination are the parameters $\alpha_j$ of linear combination obtained in step 405 and the reconstructed modulation signal SMR is computed via linear combination of the signals E1, E2, Ej, . . . , EX:

$$SMR = \Sigma_j \alpha_j Ej$$

In one or more embodiments, the signal-processing device 120 is configured, in a step 415 (called the decoding step), to compute a degree of statistical dependence between the reconstructed modulation signal and each modulation signal of the set of modulation signals and to identify at least one visual stimulus corresponding to a modulation signal for which the degree of statistical dependence is higher than a threshold SC2, of value for example comprised between 0.2 and 0.3. The fact of identifying at least one visual stimulus corresponding to a modulation signal for which the degree of statistical dependence is higher than a threshold SC2 means that the visual attention of the individual is being given, a priori, to this visual stimulus and/or that these one or more visual stimulus have just appeared in a zone of the display screen observed by the individual. It is therefore possible to use this identification to detect that a change in display has occurred and/or that a change in focus of visual attention has occurred. The degree of statistical dependence may be determined as described above in this document. The degree of statistical dependence is for example a coefficient of temporal correlation between the reconstructed modulation signal and a modulation signal of the set of modulation signals.

In one or more embodiments, the number N of visual stimuli, of modulation signals and of graphical objects is strictly higher than 1 and the signal-processing device 120 is furthermore configured, in a step 415, to seek, among the plurality of modulation signals SM1, SM2, . . . , SMN, the modulation signal SMi for which the degree of statistical dependence with the reconstructed modulation signal SMR is maximal and to identify the visual stimulus OAi corresponding to the modulation signal SMi for which the degree of statistical dependence is maximal. The visual attention is a priori focused on the identified visual stimulus OAi. The search is for example carried out by computing a degree of statistical dependence between the reconstructed modulation signal SMR and each signal of the plurality of modulation signals SM1, SM2, . . . , SMN. This decoding step may be carried out in a given moving time window, here called the decoding window, and periodically repeated for each temporal position of the decoding window. The duration of the decoding window may be identical to that of the reconstruction window.

In one or more embodiments, when the number N of visual stimuli, of modulation signals and of graphical objects is strictly higher than 1, one or more visual stimuli may be displayed at a given time on the display screen 105. The decoding step 415 may nevertheless be identical whatever the number of visual stimuli displayed at a given time, the statistical dependence being able to be sought with any one of the modulation signals SM1, SM2, . . . , SMN corresponding to the visual stimuli capable of being displayed. Thus, the need to modify dynamically and to synchronize the processing operations carried out in the decoding step 415 with respect to the variations in the content actually displayed is avoided. This may be very useful when the visual stimuli are integrated into a video or when the user interface, into which the visual stimuli are integrated, is modified dynamically as the user interacts with this user interface.

In one example embodiment, 10 visual stimuli taking the form of flashing numbers (numbers ranging from 0 to 9) are displayed on a screen, each flashing at a slightly different frequency or with the same frequency but appearing alternately on the screen. The individual is equipped with an EEG headcap and views a display screen on which the 10 numbers flash at different frequencies.

In one embodiment, during the determination of the focus of visual attention, in case of ambiguity between two or more visual stimuli or in case of perturbations and/or artefacts in the recorded EEG signals due, for example, to movements of the user, it is possible to temporarily modify (for example, during the time required to remove the ambiguity or to obtain less perturbed signals) the modulation signals of the visual stimuli. This modification may be carried out so as, for example, to display only visual stimuli for which there is ambiguity and/or to modify the modulation signals of the visual stimuli for which there is ambiguity.

The modification of the modulation signals may consist in modifying the frequency or the temporal pattern of the modulation signals, so as to increase the frequency and/or the total duration of visibility and/or the degree of transformation of the visual stimuli for which there is ambiguity and to decrease the frequency and/or the total duration of visibility and/or the degree of transformation of the other visual stimuli. The modification may also consist in permuting the modulation signals between one another, without changing their temporal pattern or their frequency. This permutation may be random. Such a permutation amounts, when the modulation signals and the elementary transformation are defined so that the visual stimuli flash by appearing and disappearing on the display screen in a given order (see the example of FIG. 2E), in modifying, for example randomly, the order of appearance of the visual stimuli, so that the stimuli for which there is ambiguity are visible more frequently. The permutation may be combined with a modification of the modulation signals with the aim of increasing the frequency and/or the total duration of visibility and/or the degree of transformation of the visual stimuli for which there is ambiguity.

The signal-processing device 120 allows, without any information other than the EEG, the visual stimulus on which attention is focused to be automatically identified. A reconstruction model allows, from the raw EEG, the reconstructed modulation signal to be generated. The modulation signal is correlated to the modulation signals corresponding to the various animated graphical objects, the observed visual stimulus being that corresponding to the modulation signal for which the degree of statistical dependence is maximal.

Tests obtained by grouping the results of a plurality of individuals allow it to be showed that the method for determining the observed visual stimulus is very robust (error rate lower than 10% for signals E1, E2, . . . , EX recorded over a time of 1 second), even when the learning phase is very short, i.e. a few minutes (for example less than 5 minutes) or even a few seconds (for example less than 5 seconds) in length, and carried out with a few stimuli types.

The method for determining the focus of visual attention is applicable not merely to numbers but also to many human-machine interfaces, and for example to a complete alphanumeric keyboard comprising 26 or more characters.

Figure 5:
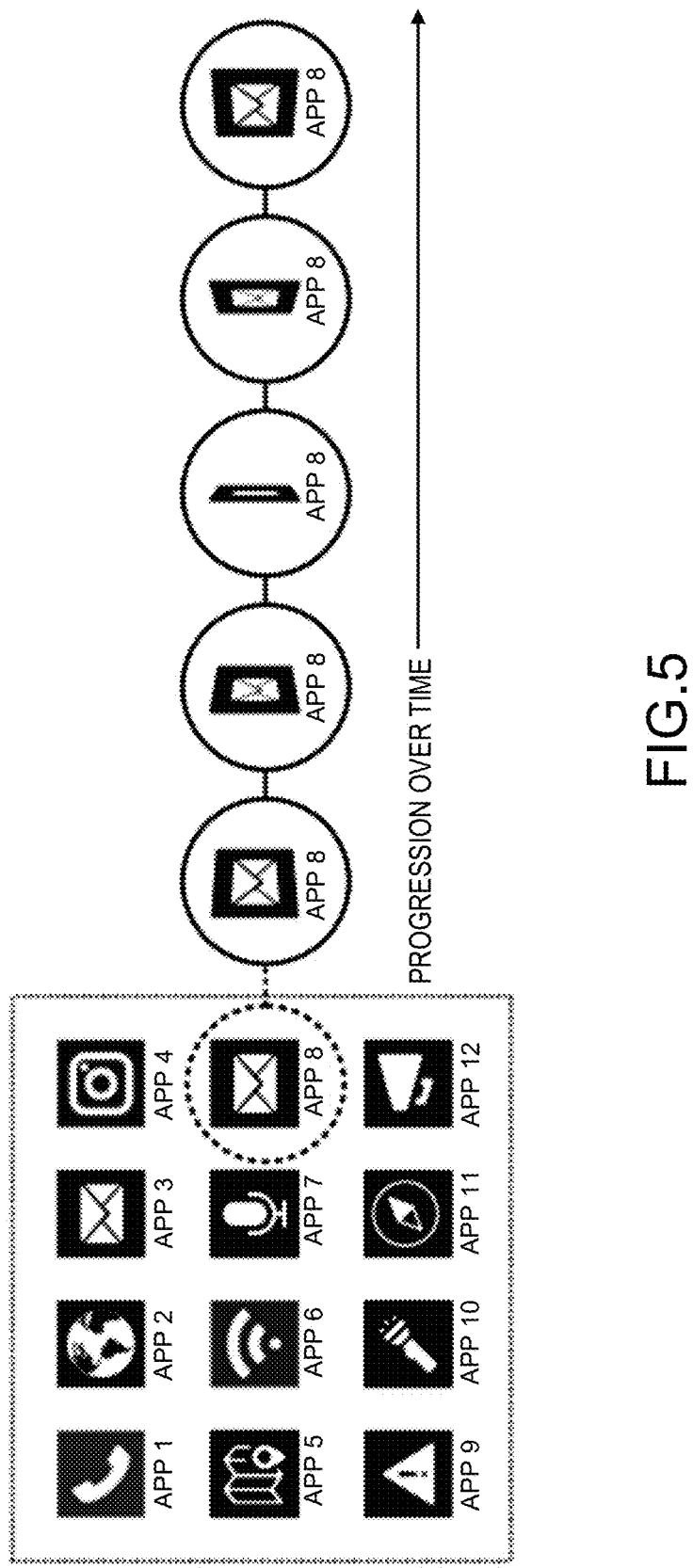
FIG. 5 illustrates an example of an animated graphical object.

FIG. 5 illustrates another example of a human-machine interface to which this method is applicable. In this example, the dynamic stimuli consist of logos or icons that are animated, not by elementary transformations that act on the light intensity of the logo, but by applying movements so as to move the logo about itself, in a plane or in a three-dimensional space. These movements are for example oscillations or rotations, at various frequencies decodable in real-time. In this case, the amplitude of the corresponding modulation signal indicates the degree of transformation at a given time, i.e. the angle of rotation to be applied at a given time. These movements are for example periodic.

In FIG. 5, 12 logos APP1 to APP12 have been shown, said logos being arranged in a grid of 4×3 logos. Although this figure has been presented in black and white, the logos may also be in color. In the example of FIG. 5, the logos pivot about themselves at various frequencies, as illustrated in FIG. 5 for the logo APP8. Each of these logos is animated by a rotational oscillation about itself that occurs at a frequency different from that of the other logos. The periodic rotation applied to the icons induces cerebral responses that are detectable in the EEG signals at the specific frequency of rotation, and which may be decoded in real-time by virtue of the techniques described above. This type of interface is highly flexible and could in particular be employed in a smart phone or tablet. Such a human-machine interface for example allows graphical interfaces to be produced for any type of computational device, for example for software applications and/or operating systems on a mobile terminal or computer, whether the display screen is a touch screen or not.

Figure 6:
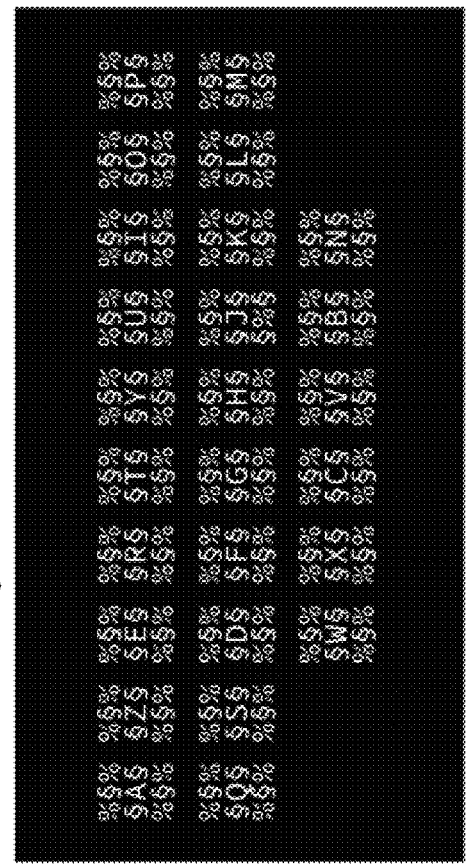
FIG. 6 shows examples of visual stimuli.
Figure 6:
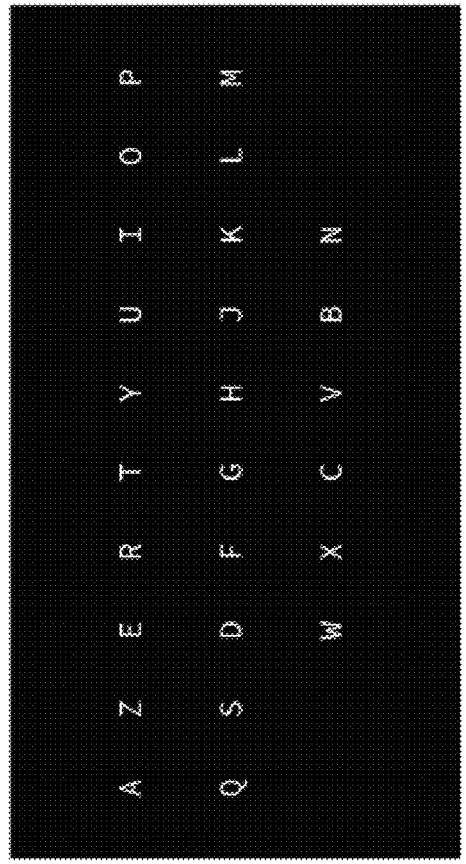

FIG. 6 illustrates another example of a usable human-machine interface. In order to facilitate the focus of the visual attention of an individual on a visual stimulus and to minimize the influence, on the EEG signals, of neighboring visual stimuli, a technique referred to as "crowding" may be called upon. This technique consists in encircling each visual stimulus with optionally animated lateral masks that decrease the visual perturbations related to the animation of neighboring visual stimuli and allow the individual to more effectively focus his attention on one stimulus in particular and the decoding thereof therefore to be improved.

Figure 7:
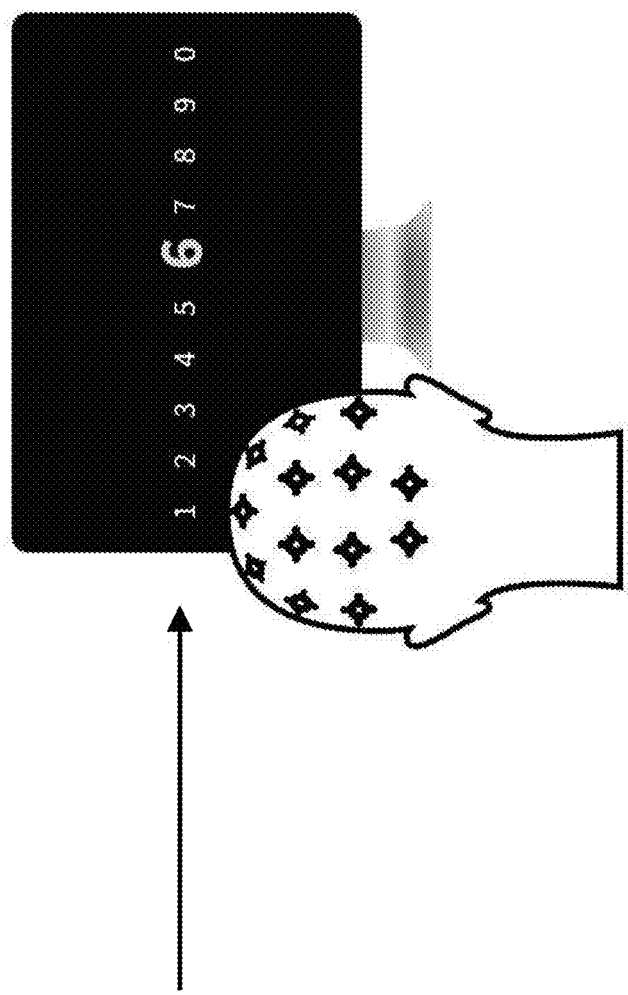
FIG. 7 illustrates an example of application of a system and method for determining the focus of visual attention.
Figure 7:
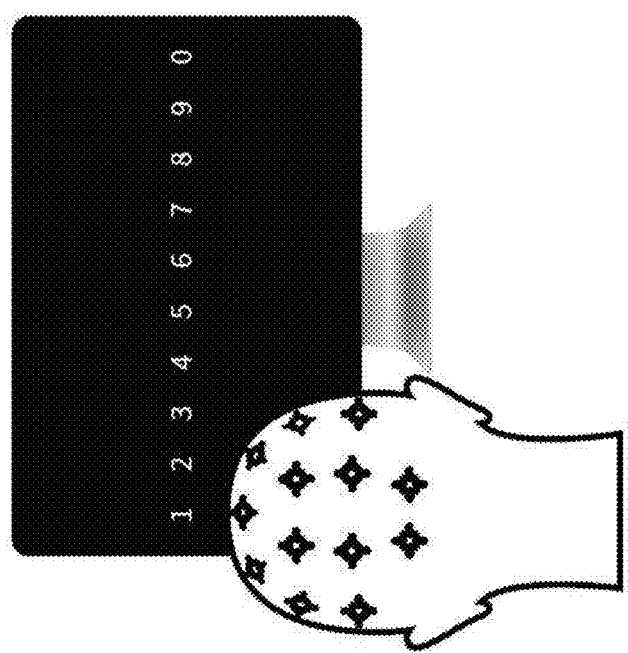

FIG. 7 illustrates another example of a human-machine interface in which feedback is given to the user on the visual stimulus that has been identified as being observed by the user. The human-machine interface comprises the numbers 0 to 9. In the example of FIG. 7, the user observes the number 6 and the feedback consists in enlarging the number identified as being observed by applying a method for determining the focus of visual attention according to the present description. Generally, the feedback given to the user may consist in highlighting the identified visual stimulus, for example, by increasing its brightness, by making it flash, by zooming into it, by changing its position, by changing its size or by changing its color, etc.

In one or more embodiments, the visual stimuli form part of a human-machine interface of a software application or of a computational device, and a command is sent to trigger the execution of one or more operations associated with the identified visual stimulus following the identification of the observed visual stimulus via implementation of a method for determining the focus of visual attention according to the present description.

In one or more embodiments, the various steps of the one or more methods described in this document are implemented by a software package or computer program.

The present description thus relates to a software package or computer program containing software instructions or program-code instructions that are readable and/or executable by a computer or by a data processor, these instructions being configured to command the execution of the steps of one or more than one of the methods described in this document when this computer program is executed by a computer or data processor.

These instructions may use any programming language, and may take the form of source code, object code, or of code intermediate between source code and object code, such as code in a partially compiled form, or in any other desirable form. These instructions are intended to be stored in a memory of a computational device or computational system, loaded then executed by a processing unit or data processor of this computational device or computational system in order to implement the steps of one or more than one of the methods described in this document. Some or all of these instructions may be stored, temporarily or indefinitely, on a non-volatile computer-readable medium of a local or remote storing device comprising one or more storage media.

The present description also relates to a data medium readable by a data processor, containing instructions of a software package or computer program such as mentioned above. The data medium may be any entity or device capable of storing such instructions. Embodiments of computer-readable media comprise, without being limited thereto, both data-storage media and communication media comprising any medium that facilitates the transfer of a computer program from one location to another. Such a storage medium may be an optical storage device such as a compact disc (CD, CD-R or CD-RW), DVD (DVD-ROM or DVD-RW) or Blu-ray disc, a magnetic medium such as a hard disk, magnetic tape or floppy disk, a removable storage medium such as a USB key, an SD or micro-SD memory card, or even a memory, such as a random-access memory (RAM), read-only memory (ROM), cache memory, non-volatile memory, back-up memory (for example flash or programmable memories), etc.

The present description also relates to a computational device or computational system comprising means for implementing the steps of one or more than one of the methods described in this document. These means are software and/or hardware for implementing the steps of one or more than one of the methods described in this document.

The present description also relates to a computational device or computational system comprising at least one memory for storing code instructions of a computer program for executing all or some of the steps of one or more than one of the methods described in this document and at least one data processor configured to execute such a computer program.

The invention claimed is:

1. A method for determining a focus of visual attention of an individual from electroencephalographic signals, the method comprising;
   generating a set of at least one visual stimulus to be displayed based on at least one graphical object of a human-machine interface of a computational device, at least one elementary transformation, and a set of at least one modulation signal, a visual stimulus of the set of at least one visual stimulus being an animated graphical object obtained by applying to a graphical object a temporal succession of elementary transformations that is temporally parameterized by a corresponding modulation signal;
   presenting the at least one visual stimulus in a display to the individual;
   recording a plurality of electroencephalographic signals produced by the individual while the individual is paying attention to the displayed at least one visual stimulus; and
   performing, in real-time, operations comprising:
      reconstructing a modulation signal from the plurality of electroencephalographic signals produced by the individual in order to obtain a reconstructed modulation signal;
      computing a degree of statistical dependence between the reconstructed modulation signal and each modulation signal of the set of at least one modulation signal;
      in response to identifying at least one visual stimulus corresponding to a modulation signal for which the degree of statistical dependence is higher than a first threshold, triggering one or more operations of the computational device.

2. The method as claimed in claim 1, wherein the set of at least one visual stimulus comprises a plurality of visual stimuli and the set of at least one modulation signal comprises a plurality of modulation signals, the method further comprising:
   searching, among the plurality of modulation signals, for a modulation signal for which a degree of statistical dependence with the reconstructed modulation signal is maximal; and
   identifying a visual stimulus corresponding to a modulation signal for which the degree of statistical dependence is maximal;
   the plurality of modulation signals being composed so that an overall degree of statistical dependence, which is determined in a time and/or frequency domain, for all pairs of the plurality of modulation signals corresponding to two separate visual stimuli, is lower than a second threshold.

3. The method as claimed in claim 1, wherein the reconstruction is carried out by applying a reconstruction model to the plurality of electroencephalographic signals.

4. The method as claimed in claim 3,
wherein the reconstruction model comprises a plurality of parameters of combinations of electroencephalographic signals, and
wherein the method further comprises determining values of parameters of the plurality of parameters of the combinations of electroencephalographic signals in an initial learning phase.

5. The method as claimed in claim 4, wherein, in the initial learning phase applied to a subset of at least one visual stimulus among the plurality of visual stimuli, the method further comprises:
obtaining, for each visual stimulus of said subset of at least one visual stimulus, a respective electroencephalographic signal of a plurality test electroencephalographic signals produced by the individual focusing attention on the each visual stimulus; and
determining optimal values for the plurality of parameters of combinations of electroencephalographic signals, for which values the application of the reconstruction model to the plurality of test electroencephalographic signals recorded for a visual stimulus allows a reconstructed modulation signal to be generated that approximates as best as possible the modulation signal corresponding to the visual stimulus in question.

6. The method as claimed in claim 1, wherein each modulation signal defines variations as a function of time in at least one parameter of application of an elementary transformation to a graphical object.

7. The method as claimed in claim 6, wherein the at least one parameter of application is a degree of transformation or a rate of application of an elementary transformation.

8. The method as claimed in claim 1, wherein an elementary transformation is a transformation of the set of transformations consisting of a variation in light intensity, a variation in contrast, a colorimetric transformation, a geometric deformation, a rotation, an oscillation, a movement along a path, a change in shape and a change in graphical object or a combination of transformations chosen from said set of transformations.

9. A system for determining a focus of visual attention of an individual from electroencephalographic signals, the system comprising;
a device for generating display signals, which is configured to:
generate a set of at least one visual stimulus to be displayed based on at least one graphical object of a human-machine interface of a computational device, at least one elementary transformation, and a set of at least one modulation signal, a visual stimulus of the set of at least one visual stimulus being an animated graphical object obtained by applying to a graphical object a temporal succession of elementary transformations that is temporally parameterized by a corresponding modulation signal; and
present the at least one visual stimulus in a display to the individual; and
a real-time signal-processing device configured to:
obtain a plurality of electroencephalographic signals produced by the individual while the individual is paying attention to the displayed at least one visual stimulus;
obtain a reconstructed modulation signal by reconstructing a modulation signal from the plurality of electroencephalographic signals;
compute a degree of statistical dependence between the reconstructed modulation signal and each modulation signal of said set of at least one modulation signal; and
in response to identifying at least one visual stimulus corresponding to a modulation signal for which the degree of statistical dependence is higher than a first threshold, trigger one or more operations of the computational device.

10. The system as claimed in claim 9, wherein the set of at least one visual stimulus comprises a plurality of visual stimuli and the set of at least one modulation signal comprises; a plurality of modulation signals, the signal-processing device furthermore being configured to;
search, among the plurality of modulation signals, for a modulation signal for which the degree of statistical dependence with the reconstructed modulation signal is maximal;
identify the visual stimulus corresponding to the modulation signal for which the degree of statistical dependence is maximal;
the plurality of modulation signals being composed so that an overall degree of statistical dependence, which is determined in a time and/or frequency domain, for all pairs of modulation signals of the set of at least one modulation signal corresponding to two separate visual stimuli, is lower than a second threshold.

11. The system as claimed in claim 9, wherein the reconstructed modulation signal is obtained by applying a reconstruction model to the plurality of electroencephalographic signals.

12. The system as claimed in claim 9, wherein each modulation signal defines variations as a function of time in at least one parameter of application of an elementary transformation to a graphical object.

13. The system as claimed in claim 12, wherein the at least one parameter of application is a degree of transformation or a rate of application of an elementary transformation.

14. A non-transitory computer-readable storage medium storing computer-executable instructions, that when executed by the computer, cause the computer to perform operations comprising:
generating a set of at least one visual stimulus to be displayed from at least one graphical object of a human-machine interface of a computational device, from at least one elementary transformation and from a set of at least one modulation signal, a visual stimulus being an animated graphical object obtained by applying to a graphical object a temporal succession of elementary transformations that is temporally parameterized by a corresponding modulation signal;
presenting the at least one visual stimulus in a display to the individual;
recording a plurality of electroencephalographic signals produced by the individual while the individual is paying attention to the displayed at least one visual stimulus; and
performing in real-time, operations comprising:
reconstructing a modulation signal from the plurality of electroencephalographic signals produced by the individual in order to obtain a reconstructed modulation signal;

computing a degree of statistical dependence between the reconstructed modulation signal and each modulation signal of the set of at least one modulation signal; and in response to identifying at least one visual stimulus corresponding to a modulation signal for which the degree of statistical dependence is higher than a first threshold, triggering one or more operations of the computational device.

15. The non-transitory computer-readable storage medium as claimed in claim 14, wherein the set of at least one visual stimulus comprises a plurality of visual stimuli and the set of at least one modulation signal comprises a plurality of modulation signals, and wherein the instructions when executed by the computer further case the computer to perform operations comprising:

searching, among the plurality of modulation signals, for a modulation signal for which a degree of statistical dependence with the reconstructed modulation signal is maximal; and identifying the visual stimulus corresponding to the modulation signal for which the degree of statistical dependence is maximal;

the modulation signals being composed so that an overall degree of statistical dependence, which is determined in a time and/or frequency domain, for all pairs of modulation signals of the plurality of modulation signals corresponding to two separate visual stimuli, is lower than a second threshold.

16. The non-transitory computer-readable storage medium as claimed in claim 14, wherein the reconstructed modulation signal is obtained by applying a reconstruction model to the plurality of electroencephalographic signals.

* * * * *

UNITED STATES PATENT AND TRADEMARK OFFICE
CERTIFICATE OF CORRECTION

PATENT NO. : 11,717,204 B2  
APPLICATION NO. : 16/645294  
DATED : August 8, 2023  
INVENTOR(S) : Kouider et al.

Page 1 of 1

It is certified that error appears in the above-identified patent and that said Letters Patent is hereby corrected as shown below:

On the Title Page

In item (72), in "Inventors", in Column 1, Line 4, delete "Arceuil" and insert --Arcueil-- therefor In the Claims In Column 20, Line 19, in Claim 1, delete "comprising;" and insert --comprising:-- therefor In Column 21, Line 48, in Claim 9, delete "comprising;" and insert --comprising:-- therefor In Column 22, Line 18, in Claim 10, delete "to;" and insert --to:-- therefor Signed and Sealed this  
Twenty-sixth Day of November, 2024

Katherine Kelly Vidal  
*Director of the United States Patent and Trademark Office*